US008188320B2

(12) United States Patent
Teles et al.

(10) Patent No.: US 8,188,320 B2
(45) Date of Patent: May 29, 2012

(54) PROCESS FOR PREPARING PURE CYCLODODECANONE

(75) Inventors: Joaquim Henrique Teles, Otterstadt (DE); Beatrice Rößler-Feigel, Weisenheim am Sand (DE); Alexander Hauk, Ludwigshafen (DE); Anton Meier, Birkenheide (DE); Christian Müller, Mannheim (DE); Michael Schelper, Ludwigshafen (DE); Tanja Kirchner, Nierstein (DE); Susanne Szeschkus, Alzey (DE); Rolf Pinkos, Bad Dürkheim (DE); Gerd-Dieter Tebben, Mannheim (DE)

(73) Assignee: BASF SE, Ludwigshafen (DE)

( * ) Notice: Subject to any disclaimer, the term of this patent is extended or adjusted under 35 U.S.C. 154(b) by 160 days.

(21) Appl. No.: 12/694,815

(22) Filed: Jan. 27, 2010

(65) Prior Publication Data
US 2010/0191018 A1 Jul. 29, 2010

(30) Foreign Application Priority Data

Jan. 28, 2009 (EP) .................................... 09151525

(51) Int. Cl.
*C07C 45/27* (2006.01)
(52) U.S. Cl. ........................................ 568/365; 568/469
(58) Field of Classification Search .................. 568/365, 568/469
See application file for complete search history.

(56) References Cited

U.S. PATENT DOCUMENTS

| 2,875,256 A | 2/1959 | Hymann |
| 3,182,093 A | 5/1965 | Wellmann |
| 3,804,914 A | 4/1974 | Fahey |
| 5,128,296 A | 7/1992 | Matson et al. |
| 5,177,278 A | 1/1993 | Sanchez |
| 5,180,870 A | 1/1993 | Paciello |
| 5,210,349 A | 5/1993 | Matson et al. |
| 5,321,176 A | 6/1994 | Sanchez |
| 7,683,214 B2 | 3/2010 | Hahn et al. |
| 2003/0065234 A1 | 4/2003 | Wohrle |
| 2008/0255393 A1 | 10/2008 | Teles et al. |
| 2010/0190869 A1 | 7/2010 | Teles et al. |
| 2010/0191018 A1 | 7/2010 | Teles et al. |
| 2010/0256398 A1 | 10/2010 | Pinkos et al. |
| 2011/0087038 A1 | 4/2011 | Teles et al. |
| 2011/0137077 A1 | 6/2011 | Teles et al. |
| 2011/0152576 A1 | 6/2011 | Teles et al. |
| 2011/0269996 A1 | 11/2011 | Teles et al. |

FOREIGN PATENT DOCUMENTS

| CA | 1070711 | 1/2008 |
| DE | 1 230 023 B | 12/1966 |
| DE | 1283836 B | 11/1968 |
| DE | 2519817 A1 | 11/1976 |
| DE | OS 25 19 817 | 11/1976 |
| DE | 10 2004 046 167.8 | 4/2006 |
| EP | 0158229 A1 | 10/1985 |
| EP | 0279397 A1 | 8/1988 |
| EP | 0285420 A1 | 10/1988 |
| EP | 1288181 | 3/2003 |
| EP | 08 153 952.0 | 4/2008 |
| EP | 09 151 002.4 | 1/2009 |
| EP | 08 153 953.8 | 9/2009 |
| WO | WO-2005/030690 A2 | 4/2005 |
| WO | WO-2006/032502 A1 | 3/2006 |
| WO | WO-2007/060160 A2 | 5/2007 |
| WO | WO 2007/104650 | 9/2007 |
| WO | WO-2008/000754 A1 | 1/2008 |
| WO | WO-2008/000756 A1 | 1/2008 |
| WO | WO-2008/000757 A1 | 1/2008 |
| WO | WO-2008/071632 A2 | 6/2008 |
| WO | WO 2009/092682 | 7/2009 |
| WO | WO 2009/092683 | 7/2009 |
| WO | WO 2009/121706 | 10/2009 |
| WO | WO 2009/121707 | 10/2009 |
| WO | WO 2010/083978 | 7/2010 |

OTHER PUBLICATIONS

Ullmann's Encyclopedia of Industrial Chemistry—Cyclododecatriene, Cyclooctadiene, and 4-Vinylcyclohexene, Oenbrink, (2012) pp. 37-40.
Weber et al, Zur Bildungsweise von cis, trans, trans-Cyclododecatrien-(1.5.9) Mittels Titanhaltiger Ziegler-Katalysatoren, (1964) pp. 10-20.
Warwel et al., Eine einfache Synthese makrocyclischer Kohlenwasserstoffe durch Metathese von Cycloolefinen, (Oct. 1987) pp. 935 -937.
Dzhemilev et al., Synthesis and Transformations of trans-1,5,9,13-Cyclohexadecatetraene, (1975), cover & pp. 41-43.
Fahey, Selective Hydrogenation of 1,5,9-Cyclododecatriene to Cyclododecene Catalyzed by Ruthenium Complexes, J. Org. Chem., vol. 38, No. 1, 1973—pp. 80-87.

*Primary Examiner* — Sikarl Witherspoon
(74) *Attorney, Agent, or Firm* — Connolly Bove Lodge & Hutz LLP

(57) ABSTRACT

The present invention relates to a process for preparing at least one cyclic compound with Z cycles and 7 to 16 carbon atoms with a keto group, at least comprising the stages:
(a1) oxidation of a composition (A), at least comprising one cyclic olefin with Z cycles and 7 to 16 carbon atoms and at least two C—C double bonds, by means of dinitrogen monoxide to give a composition (A1),
(a2) separating off the at least one cyclic olefin with Z cycles and 7 to 16 carbon atoms with at least two C—C double bonds from the composition (A1) in order to obtain a composition (A2), and
(b) distillative treatment of the composition (A2) from step (a2) in order to obtain a composition (B), comprising
   the at least one cyclic compound with Z cycles and 7 to 16 carbon atoms with a keto group and
   less than 1.0% by weight of the at least one compound with Z-1 cycles and 7 to 16 carbon atoms with at least one aldehyde group,
where Z can be 1, 2, 3 or 4.

10 Claims, No Drawings

PROCESS FOR PREPARING PURE CYCLODODECANONE

CROSS REFERENCE TO RELATED APPLICATIONS

This application claims priority to EP 09 151 525.4 filed Jan. 28, 2009, the content of which is hereby incorporated by reference.

The present invention relates to a process for preparing at least one cyclic compound with Z cycles and 7 to 16 carbon atoms with a keto group, at least comprising the stages (a1) oxidation of a composition (A), at least comprising one cyclic olefin with Z cycles and 7 to 16 carbon atoms and at least two C—C double bonds, by means of dinitrogen monoxide to give a composition (A1), at least comprising the at least one cyclic compound with Z cycles and 7 to 16 carbon atoms with a keto group, the at least one cyclic olefin with Z cycles and 7 to 16 carbon atoms with at least two C—C double bonds and at least one compound with Z−1 cycles and 7 to 16 carbon atoms with at least one aldehyde group, (a2) separating off the at least one cyclic olefin with Z cycles and 7 to 16 carbon atoms with at least two C—C double bonds from the composition (A1) from stage (a1) in order to obtain a composition (A2), at least comprising the at least one cyclic compound with Z cycles and 7 to 16 carbon atoms with a keto group and at least one compound with Z−1 cycles and 7 to 16 carbon atoms with at least one aldehyde group, and (b) distillative treatment of the composition (A2) from step (a2) in order to obtain a composition (B), comprising the at least one cyclic compound with Z cycles and 7 to 16 carbon atoms with a keto group and less than 1.0% by weight of the at least one compound with Z−1 cycles and 7 to 16 carbon atoms with at least one aldehyde group, where Z can be 1, 2, 3 or 4.

WO 2008/000757 A1 discloses a process for preparing a cyclic ketone with 7 to 16 carbon atoms, at least comprising the stages (a) oxidation of a composition (I), at least comprising one cyclic olefin with 7 to 16 carbon atoms with at least one C—C double bond, by means of nitrogen monoxide to give a composition (A), (b) treating the composition (A) with at least one base to give a composition (B). This document does not disclose that prior to the treatment of the composition (A) with at least one base in step (b), the composition obtained from the oxidation should be purified by distillation.

WO 2008/000756 A1 discloses a process for preparing a cyclic ketone with 7 to 16 carbon atoms, at least comprising the stages (a) oxidation of a composition (I), at least comprising one cyclic olefin with 7 to 16 carbon atoms with at least one C—C double bond, by means of dinitrogen monoxide to give a composition (A), (b) treatment of the composition (A) with at least one base to give a composition (B), (c) hydrogenation of the composition (B) in the presence of at least one catalyst to give a composition (C), (d) purification of the composition (C), at least comprising the steps (di) thermal treatment of the composition (C) with at least one acid, or at least one catalyst which comprises at least one transition metal, (dii) further purification by a process selected from the group consisting of distillation, extraction and crystallization. This document also does not disclose that the reaction mixture obtained from the oxidation is purified by distillation in order to reduce the content of specific by-products formed during the oxidation.

WO 2005/030690 A2 discloses a process for preparing a ketone, in particular cyclodecanone, where cyclododecatriene is reacted with dinitrogen monoxide to give cyclododecadienone, and the resulting cyclododecadienone is hydrogenated in particular to cyclododecanone. This document does not disclose a process for preparing cyclic ketones in which the reaction mixture which is obtained from the oxidation with dinitrogen monoxide is purified by distillation in order to reduce the content of specific by-products formed during the oxidation.

WO 2008/000754 A1 discloses a process for purifying a composition (I), at least comprising one cyclic ketone with 7 to 16 carbon atoms, comprising the thermal treatment of the composition (I) with a catalyst which comprises at least one transition metal, and further purification by a process selected from distillation, extraction and crystallization. The cited document does not disclose a process for preparing cyclic ketones with 7 to 16 carbon atoms by oxidation of a corresponding olefin with dinitrogen monoxide in which the reaction mixture obtained from the oxidation is purified by distillation in order to reduce the content of specific by-products formed during the oxidation.

The processes for preparing cyclic ketones known from the prior art are still in need of improvement as regards the purity of the prepared cyclic ketones. One disadvantage of the processes of the prior art is, for example, that if the by-products formed during the oxidation are not removed completely or virtually completely, they interfere in the subsequent steps, or are converted to compounds which cannot be separated off from the desired product in a final purification step, for example a distillation, since the impurities present in the cyclic ketones, for example aldehydes, are only removed with difficulty by conventional purification processes such as distillation, extraction or recrystallization since the functional groups and the number of carbon atoms are similar. This is problematical in so far as cyclic ketones are required for various applications in high purity. Thus, for example, cyclododecanone is an important intermediate for the preparation of, for example, lauryllactam, dodecanedicarboxylic acid and polyamides derived therefrom, such as, for example, nylon 12 or nylon 6,12. Consequently, in these cases, a very complex purification, for example by multistage distillation and/or crystallization, is required. These purification processes are consequently complex and cost-intensive.

It is therefore an object of the present invention to provide a process with which cyclic ketones with 7 to 16 carbon atoms can be obtained in particularly high purity. It is a further object of the present invention that existing plants and/or apparatuses can be further utilized for preparing cyclic ketones with 7 to 16 carbon atoms in order to keep the additional apparatus construction to a minimum.

These objects are achieved according to the invention by a process for preparing at least one cyclic compound with Z cycles and 7 to 16 carbon atoms with a keto group, at least comprising the stages:

(a1) oxidation of a composition (A), at least comprising one cyclic olefin with Z cycles and 7 to 16 carbon atoms and at least two C—C double bonds, by means of dinitrogen monoxide to give a composition (A1), at least comprising
    the at least one cyclic compound with Z cycles and 7 to 16 carbon atoms with a keto group,
    the at least one cyclic olefin with Z cycles and 7 to 16 carbon atoms with at least two C—C double bonds and
    at least one compound with Z−1 cycles and 7 to 16 carbon atoms with at least one aldehyde group, (a2) separating off the at least one cyclic olefin with Z cycles and 7 to 16 carbon atoms with at least two C—C double bonds from the composition (A1) from stage (a1) in order to obtain a composition (A2), at least comprising
    the at least one cyclic compound with Z cycles and 7 to 16 carbon atoms with a keto group and at least one compound with Z−1 cycles and 7 to 16 carbon atoms with at least one aldehyde group, and
(b) distillative treatment of the composition (A2) from step (a2) in order to obtain a composition (B), comprising
the at least one cyclic compound with Z cycles and 7 to 16 carbon atoms with a keto group and
less than 1.0% by weight of the at least one compound with Z−1 cycles and 7 to 16 carbon atoms with at least one aldehyde group,
where Z can be 1, 2, 3 or 4.

Surprisingly, it has been found that in particular by-products such as cyclic and open-chain aldehydes which have one cycle less (Z−1 cycles) than the starting compounds used, or if appropriate also by-products which comprise keto groups, can generally be selectively depleted from a mixture with cyclic ketones with the same number or a similar number of carbon atoms by purifying the mixture obtained from the oxidation, following the removal of remaining starting material, by distillation in order to reduce the content of these troublesome by-products. By removing the specified compounds directly after the oxidation, it is possible to obtain the desired end product, the at least one cyclic compound with Z cycles and 7 to 16 carbon atoms with a keto group, in particularly high purity which is not accessible without step (b) according to the invention.

Furthermore, the distillative removal of the specified compounds in step (b) of the process according to the invention can suppress the formation of troublesome compounds which cannot be separated off completely from the desired product.

By means of the process according to the invention it is possible to obtain cyclic compounds with 7 to 16 carbon atoms and a keto group with a purity of, for example, at least 95%, preferably at least 98%. The purity can be determined by all processes known to the person skilled in the art, for example gas chromatography. A further advantage of the process according to the invention is that it can easily be combined with existing plants, meaning that no cost-intensive modifications are required.

Stage (a1)
(a1) oxidation of a composition (A), at least comprising one cyclic olefin with Z cycles and 7 to 16 carbon atoms and at least two C—C double bonds, by means of dinitrogen monoxide to give a composition (A1), at least comprising
the at least one cyclic compound with Z cycles and 7 to 16 carbon atoms with a keto group,
the at least one cyclic olefin with Z cycles and 7 to 16 carbon atoms with at least two C—C double bonds and
at least one compound with Z−1 cycles and 7 to 16 carbon atoms with at least one aldehyde group.

The reaction according to stage (a1) can in general take place according to all process procedures in which the olefin and dinitrogen monoxide react with one another.

In stage (a1) of the process according to the invention, the cyclic olefin is oxidized by reaction with dinitrogen monoxide. Here, for the reaction of the cyclic olefin with dinitrogen monoxide, at least one suitable solvent or diluent can be used. Ones which may be mentioned are inter alia cyclic alkanes, for example cyclododecane or cyclododecanone or saturated aliphatic or aromatic, optionally alkyl-substituted hydrocarbons, where essentially all customary solvents and/or diluents are suitable with the proviso that they have neither a C—C double bond, nor a C—C triple bond, nor an aldehyde group.

In general, the addition of a solvent or diluent is not necessary in the reaction of the cyclic olefin with dinitrogen monoxide.

The temperature during the reaction of the cyclic olefin with dinitrogen monoxide is preferably 140 to 350° C., further preferably 180 to 320° C. and particularly preferably 200 to 300° C.

It is possible to carry out the reaction of the cyclic olefin with dinitrogen monoxide at two or more temperatures or in two or more temperature ranges which are in each case within the limits stated above. Temperature changes in the course of the reaction can be completed continuously or discontinuously.

The pressure during the reaction of the cyclic olefin with dinitrogen monoxide is preferably higher than the autogonous pressure of the starting material mixture and/or product mixture at the selected reaction temperature or the selected reaction temperatures. The pressure is preferably 1 to 1000 bar, further preferably 40 to 325 bar and particularly preferably 50 to 200 bar.

It is possible to carry out the reaction of the cyclic olefin with dinitrogen monoxide at two or more pressures and/or in two or more pressure ranges which are in each case within the limits stated above. Pressure changes in the course of the reaction can be completed continuously or discontinuously.

There are no particular restrictions as regards the reactors which can be used for the reaction of the cyclic olefin with dinitrogen monoxide. In particular, the reaction can take place in batch mode or in continuous mode. Accordingly, reactors which can be used are, for example, at least one CSTR (Continuous Stirred Tank Reactor) with at least one internal and/or at least one external heat exchanger, at least one tubular reactor, at least one tube-bundle reactor or at least one loop reactor. It is likewise possible to configure at least one of these reactors such that it has at least two different zones. Such zones can differ, for example, in reaction conditions such as, for example, the temperature or the pressure and/or in the geometry of the zone, such as, for example, the volume or the cross section. If the reaction is carried out in two or more reactors, two or more identical reactor types or at least two different reactor types may be used.

Preferably, the reaction of the cyclic olefin with dinitrogen monoxide is carried out in a single reactor. For example, the reaction is preferably in continuous mode. A suitable reactor is described, for example, in the as yet unpublished patent application EP 09151002.4.

The residence time of the reaction material in the at least one reactor during the reaction of the cyclic olefin with dinitrogen monoxide is generally in the range up to 20 hours, preferably in the range from 0.1 to 20 hours, further preferably in the range from 0.2 to 15 hours and particularly preferably in the range from 0.25 to 10 hours.

In the feed which is fed to the reaction of dinitrogen monoxide with the cyclic olefin, the molar ratio of dinitrogen monoxide and the cyclic olefin is generally in the range from 0.05 to 4, preferably in the range from 0.06 to 1, further preferably in the range from 0.07 to 0.5 and particularly preferably in the range from 0.1 to 0.4.

The reaction of the cyclic olefin with Z cycles and 7 to 16 carbon atoms with at least two C—C double bonds with dinitrogen monoxide can be carried out such that at a very high selectivity with regard to the at least one cyclic compound with Z cycles and 7 to 16 carbon atoms with a keto group, a conversion of the cyclic olefin in the range up to 50%, preferably in the range from 5 to 30% and particularly preferably in the range from 10 to 20%, is achieved. Here, the selectivity, based on the at least one cyclic compound with Z cycles 7 to 16 carbon atoms and a keto group, is generally at least 90%, preferably at least 92.5% and particularly preferably at least 93%.

In principle, according to the invention, any cyclic olefin with Z cycles and 7 to 16 carbon atoms with at least two C—C double bonds or any mixture of two or more different cyclic olefins with Z cycles 7 to 16 carbon atoms with in each case at least two C—C double bonds can be reacted with dinitrogen monoxide.

According to the invention, the formulation "Z cycles" means that the correspondingly described compounds have cyclic units in a number of Z. According to the invention, Z is 1, 2, 3 or 4, for example for the preferred compounds (I) to (VIII) and (XI Z is 1, for the preferred compounds (IX) and (X), Z is 2.

Preferably, according to the invention, the cyclic olefin has two, three or four C—C double bonds.

Consequently, according to a further embodiment, the present invention also relates to a process as described above for preparing a cyclic compound with Z cycles and 7 to 16 carbon atoms with a keto group, where the cyclic olefin has three C—C double bonds.

The present invention also relates to the process according to the invention where the at least one cyclic olefin with two or more C—C double bonds is selected from the group consisting of 1,5-cyclooctadiene, 1,5-cyclododecadiene. 1,9-cyclohexadecadiene, 1,8-cyclotetradecadiene, 1,6-cyclodecadiene, 1,6,11-cyclopentadecatriene, 1,5,9-cyclododecatriene, vinylcyclohexene and mixtures thereof. These specified olefins which can be used according to the invention have one cycle, thus in these cases Z is one. Further preferred compounds are norbornadiene and ethylidenenorbornene in which Z is two.

1,5-Cyclooctadiene (I), 1,5-cyclododecadiene (II), 1,9-cyclohexadecadiene (III), 1,8-cyclotetradecadiene (IV), 1,6-cyclododecadiene (V), 1,6,11-cyclopentadecatriene (VI), 1,5, 9-cyclododecatriene (VII), 1,5,9,13-cyclohexadecatetraene (VII), norbornadiene (IX), ethylidenenorbornene (X), vinylcyclohexene (XI), where always only one of the possible isomers is shown, are depicted below:

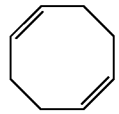
(I)

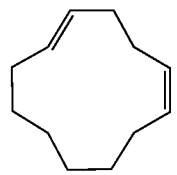
(II)

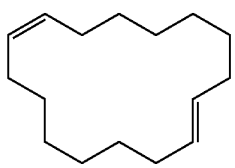
(III)

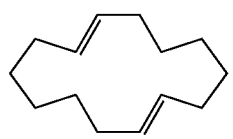
(IV)

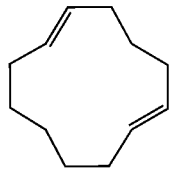
(V)

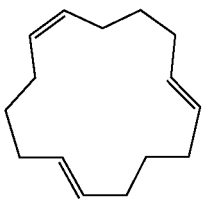
(VI)

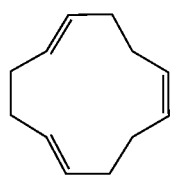
(VII)

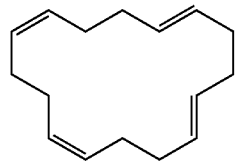
(VIII)

(IX)

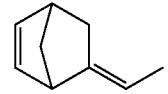
(X)

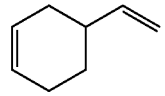
(XI)

The cyclic olefin used is particularly preferably 1,5,9-cyclododecatriene (VII). 1,5,9-Cyclododecatriene can in general be used in any possible isomer, for example cis,trans,trans-1,5,9-cyclododecatriene, cis,cis,trans-1,5,9-cyclododecatriene, all-trans-1,5,9-cyclododecatriene or all-cis-1,5,9-cyclododecatriene, very particularly preferably cis, trans,trans-1,5,9-cyclododecatriene. In the process according to the invention, it is also possible to react a mixture of the specified isomers and in particular an isomer mixture which comprises predominantly cis,trans,trans-1,5,9-cyclododecatriene.

Consequently, in one preferred embodiment, the present invention relates to a process for preparing a ketone as described above, where the cyclic olefin with Z cycles and 7 to 16 carbon atoms with at least two double bonds is cyclododecatriene, preferably 1,5,9-cyclododecatriene, particularly preferably cis,trans,trans-1,5,9-cyclododecatriene.

The cyclododecatriene preferably used in the process according to the invention can generally be obtained by all processes known to the person skilled in the art. In one preferred embodiment, the cyclododecatriene is obtained by trimerization of butadiene.

Consequently, according to one further embodiment, the present invention also relates to a process as described above for preparing a cyclic ketone with Z cycles and 7 to 16 carbon atoms with a keto group, where the cyclic olefin with Z cycles and 7 to 16 carbon atoms with at least two double bonds is cyclododecatriene which has been prepared from butadiene by means of trimerization.

1,5,9-Cyclododecatriene can be prepared, for example, by trimerization of pure 1,3-butadiene, as is described, for example, in T. Schiffer. G. Oenbrink, "Cyclododecatriene, Cyclooctadiene, and 4-Vinylcyclohexene", in Ullmann's Encyclopedia of Industrial Chemistry, 6th Edition (2000), Electronic Release, Wiley VCH, pages 1 to 4. Within the framework of this process, for example in the case of trimerization in the presence of Ziegler catalysts, cis,trans,trans-1,5,9-cyclododecatriene, cis,cis,trans-1,5,9-cyclododecatriene and all-trans-1,5,9-cyclododecatriene are formed, as is described, for example, in H. Weber et al. "Zur Bildungsweise von cis,trans,trans-Cyclododecatrien-(1.5.9) mittels titanhaltiger Katalysatoren [The mode of formation of cis,trans,trans-cyclododecatriene-(1,5,9) by means of titanium-containing catalysts]" in Liebigs Ann. Chem. 681 (1965) pages 10 to 20. Cyclododecatriene can be prepared, for example, by trimerization of 1,3-butadiene using a titanium or nickel catalyst, for example in accordance with DE 1283836.

Whereas in principle all suitable titanium catalysts can be used for the trimerization, the titanium tetrachloride/ethylaluminum sesquichloride catalyst described in the article by Weber et al. is particularly suitable.

Whereas in principle all suitable nickel catalysts can be used for the trimerization, the bis-cyclooctadienylnickel/ethoxydiethylaluminum catalyst described in DE 1283836 is particularly suitable.

The butadiene used for the trimerization particularly preferably has a degree of purity, determined by gas chromatography, of at least 99.6% and further preferably of at least 99.65%. Within the detection accuracy, the 1,3-butadiene used particularly preferably comprises no 1,2-butadiene and no 2-butyne.

This trimerization generally produces mixtures which comprise at least 95% by weight, preferably at least 96% by weight and further preferably at least 97% by weight, of cis,trans,trans-1,5,9-cyclododecatriene. The mixtures particularly preferably comprise about 98% by weight of cis, trans,trans-1,5,9-cyclododecatriene. This mixture comprising cis,trans,trans-1,5,9-cyclododecatriene can be used as such for the reaction according to the invention in accordance with stage (a). It is likewise possible, via at least one suitable method, for example preferably via at least one distillation, to separate off the cis,trans,trans-1,5,9-cyclododecatriene from the mixture and to use it in the reaction in accordance with stage (a).

According to a very particularly preferred embodiment of the process according to the invention, the cyclododecatriene used is an isomer mixture which comprises predominantly cis,trans,trans-1,5,9-cyclododecatriene, trans,trans,trans-1,5,9-cyclododecatriene or cis,cis,trans-1,5,9-cyclododecatriene. Preference is given to using an isomer mixture which comprises more than 60% by weight, based on the isomer mixture, of cis,trans,trans-1,5,9-cyclododecatriene, further preferably more than 70% by weight, in particular more than 80% by weight, particularly preferably more than 90% by weight, for example more than 91% by weight, more than 92% by weight, more than 93% by weight, more than 94% by weight, more than 95% by weight, more than 96% by weight, more than 97% by weight or more than 98% by weight.

The olefins which can be used according to the invention can be prepared, for example, by the processes specified in the following literature references:

(I) Cycloocta-1,5-diene is produced as by-product in the synthesis of compound (VII), as is described, for example, in T. Schiffer, G. Oenbrink, "Cyclododecatriene, Cyclooctadiene, and 4-Vinylcyclohexene", in Ullmann's Encyclopedia of Industrial Chemistry, 6th Edition (2000), Electronic Release, Wiley VCH.

(II) Cyclododeca-1,5-diene can be obtained, for example, by catalytic reduction of compound (VII), as is described, for example, in U.S. Pat. No. 3,182,093.

(III) Cyclohexadeca-1,9-diene can be obtained by metathesis of cyclooctene, as is described, for example, in EP 1288181.

(IV) Cyclotetradeca-1,8-diene can be obtained by metathesis of cycloheptene, as is described, for example, in S. Warwel, H. Kaetker, Synthesis (1987) (10), 935-7.

(V) Cyclodeca-1,6-diene, preferably the cis,cis isomer, can be obtained by isomerization of cis,trans-cyclodeca-1,5-diene, as is described, for example, in DE 1 230 023.

(VI) Cyclopentadecadeca-1,6,11-triene can be obtained by cyclooligomerization of cyclopentene, as is described, for example, in DD 115480.

(VII) See (I).

(VIII) Cyclohexadeca-1,5,9,13-tetraene can be obtained by tetramerization of butadiene, as is described, for example, in U. M. Dzhemilev, L. Yu. Gubaidullin, G. A. Tolstikov, Zhurnal Organicheskoi Khimii (1976), 12(1), 44-6.

(IX) Norbornadiene can be obtained by reacting cyclopentadiene with acetylene, as is described, for example, in U.S. Pat. No. 2,875,256.

(X) Ethylidenenorbornene can be obtained by base-catalyzed rearrangement of 5-vinyl-2-norbornene, as is described, for example, in EP 0 279 397.

(XI) 4-Vinylcyclohexene can be prepared by Diels-Alder reaction of butadiene with itself, but is also produced as a by-product in the preparation of compound (VII), as is described, for example, in T. Schiffer, G. Oenbrink, "Cyclododecatriene, Cyclooctadiene, and 4-Vinylcyclohexene", in Ullmann's Encyclopedia of Industrial Chemistry, 6th Edition (2000), Electronic Release, Wiley VCH, pages 1-4.

The reaction according to the invention of composition (A), at least comprising one cyclic olefin with Z cycles and 7 to 16 carbon atoms and at least two C—C double bonds, produces, by means of dinitrogen monoxide, a composition (A1), at least comprising the at least one cyclic compound with Z cycles and 7 to 16 carbon atoms with a keto group, the at least one cyclic olefin with Z cycles and 7 to 16 carbon atoms with at least two C—C double bonds and at least one compound with Z−1 cycles and 7 to 16 carbon atoms with at least one aldehyde group.

In general, the preferred reaction according to the invention of cis,trans,trans-1,5,9-cyclododecatriene with dinitrogen monoxide according to stage (a1) results in a cyclododeca-4,8-dienone isomer mixture which comprises at least two of the isomers cis,trans-cyclododeca-4,8-dienone, trans,cis-cyclododeca-4,8-dienone and trans,trans-cyclododeca-4,8-dienone as cyclic compounds with Z cycles and 7 to 16 carbon atoms with a keto group.

According to the invention, an isomer mixture is preferably obtained in which trans,cis and cis,trans isomers are formed in approximately equal amounts, and the trans,trans isomer is formed in only small amounts compared to the two other isomers. Accordingly, an isomer mixture typical for example has the specified isomers in molar ratios of about 1:1:0.08.

The at least one cyclic compound with Z cycles and 7 to 16 carbon atoms with a keto group present in composition (A1) is the desired product of stage (a) of the process according to the invention. Since preferably the substrate used is at least one cyclic compound with Z cycles and 7 to 16 carbon atoms and three double bonds, the particularly preferred product formed in stage (a) of the process according to the invention through oxidation of one of these double bonds is at least one cyclic compound with Z cycles and 7 to 16 carbon atoms with two double bonds and one keto group. In a further preferred embodiment, this product from stage (a) is converted by a hydrogenation in a subsequent stage to at least one saturated cyclic compound with Z cycles and 7 to 16 carbon atoms and a keto group, in particular cyclododecanone.

Within the context of the present invention, the composition (A1) comprises at least one cyclic compound with Z cycles and 7 to 16 carbon atoms with a keto group in an amount of in general more than 5% by weight, preferably more than 10% by weight, preferably 10 to 90% by weight, in particular 11 to 50% by weight, particularly preferably 12 to 40% by weight, especially preferably 13 to 30% by weight, for example 14 to 20% by weight or 15 to 18% by weight.

According to the invention, also at least
  the at least one cyclic olefin with Z cycles and 7 to 16 carbon atoms with at least two C—C double bonds and
  at least one compound with Z−1 cycles and 7 to 16 carbon atoms with at least one aldehyde group.
are present in composition (A1).

The at least one cyclic olefin with Z cycles and 7 to 16 carbon atoms with at least two C—C double bonds which is present in composition (A1) is the same compound which has been used as starting compound in composition (A) before the oxidation. The at least one cyclic olefin with Z cycles and 7 to 16 carbon atoms with at least two C—C double bonds in composition (A1) is thus remaining starting material which has not been oxidized in stage (a1) of the process according to the invention. According to the invention, the at least one cyclic olefin with Z cycles and 7 to 16 carbon atoms with at least two double bonds in composition (A1) can be present in the same isomeric structures in which it has been used as starting material. In one preferred embodiment, a somewhat different isomer ratio is present in composition (A1) with regard to the at least one olefin with Z cycles and 7 to 16 carbon atoms with at least two C—C double bonds than in the starting material used in step (a1). The reason for this is, for example, the differing reactivities of the individual isomers; for example the all-trans isomer reacts more rapidly than the cis,trans,trans isomer, and this in turn reacts somewhat more quickly than the cis,cis,trans isomer.

The at least one compound with Z−1 cycles and 7 to 16 carbon atoms with at least one aldehyde group present in the composition (A1) is formed from the olefin having at least two double bonds used as starting material by oxidative cleavage of one double bond.

Since, as described above, Z describes the number of cycles present in the specified compounds, the formulation "Z−1 cycles" means that in the compounds thus described, one cycle less is present than in the compounds which comprise Z cycles. According to the invention, a compound can, for example, comprise one cycle less than the starting material as a result of a ring-opening reaction.

In stage (a1) of the process according to the invention, if appropriate also at least one compound with Z cycles and 7 to 16 carbon atoms with at least one aldehyde group is formed as by-product. This at least one by-product has the same number of cycles as the starting material used in stage (a1). This at least one compound is preferably a cyclic compound with at least one aldehyde group which is formed by ring contraction.

The at least one compound with Z−1 cycles and 7 to 16 carbon atoms with at least one aldehyde group is present in the composition (A) in general in an amount of from 0.1 to 50.0% by weight, preferably 0.5 to 10.0% by weight, particularly preferably 1.0 to 5.0% by weight.

For the preferred case where 1,5,9-cyclododecatriene, in particular cis,trans,trans-1,5,9-cyclododecatriene (Z=1), is used in the process according to the invention as starting material, the at least one compound with Z−1 cycles and 7 to 16 carbon atoms with at least one aldehyde group obtained is particularly preferably an isomer mixture of acyclic compounds with an aldehyde group and three double bonds, for example a mixture of 4,8,11-dodecatrienals, such as a mixture of cis,trans, trans,cis, trans,trans isomers, for example in the approximate ratio of 50:45:5. The cis,trans isomer is depicted as compound (XIII).

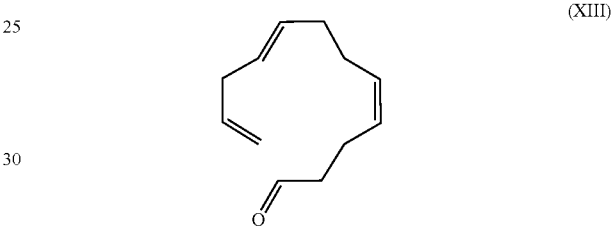

(XIII)

For this preferred case where Z is one for the starting material, the at least one compound with Z−1 cycles and 7 to 16 carbon atoms and at least one aldehyde function has no cycle since the following applies for Z−1: 1−1=0.

In one preferred embodiment of the process according to the invention, the composition (A1) obtained in stage (a1) additionally comprises at least one cyclic compound with Z cycles and 7 to 16 carbon atoms with at least two keto groups. This compound is formed from the olefin with at least two double bonds used as starting material by oxidizing two of the double bonds present with dinitrogen monoxide. In one preferred embodiment, this at least one cyclic compound with Z cycles and 7 to 16 carbon atoms with at least two keto groups is present in the composition (A1) in general in an amount of from 0.1 to 20.0% by weight, preferably 0.5 to 10.0% by weight, particularly preferably 1.0 to 5.0% by weight.

For the particularly preferred case where 1,5,9-cyclododecatriene, in particular cis,trans,trans-1,5,9-cyclododecatriene, is used in the process according to the invention as starting material, the at least one cyclic compound with Z cycles and 7 to 16 carbon atoms with at least two keto groups obtained is particularly preferably an isomer mixture of cyclic compounds with two keto functions and a double bond, in particular cyclododecenediones, for example a mixture of 8-cis-cyclodecene-1,5-dione, 9-cis-cyclododecene-1,6-dione, 8-cis-cyclododecene-1,4-dione, 8-trans-cyclododecene-1,5-dione, 8-trans-cyclododecene-1,4-dione and ±9-trans-cyclododecene-1,6-dione isomers, for example in the approximate ratio of 38:19:19:12:6:6. 8-cis-Cyclododecene-1,5-dione isomer, which is formed as the main isomer, is depicted as compound (XII).

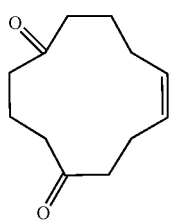

(XII)

In one preferred embodiment, the present invention thus relates to the process according to the invention comprising at least the following stages:

(a1) oxidation of a composition (A), at least comprising one cyclic olefin with Z cycles and 7 to 16 carbon atoms and at least two C—C double bonds, by means of dinitrogen monoxide to give a composition (A1), at least comprising
   the at least one cyclic compound with Z cycles and 7 to 16 carbon atoms with a keto group,
   at least one cyclic compound with Z cycles and 7 to 16 carbon atoms with at least two keto groups,
   the at least one cyclic olefin with Z cycles and 7 to 16 carbon atoms with at least two C—C double bonds and
   at least one compound with Z−1 cycles and 7 to 16 carbon atoms with at least one aldehyde group, (a2) separating off the at least one cyclic olefin with Z cycles and 7 to 16 carbon atoms with at least two C—C double bonds from the composition (A1) from stage (a1) in order to obtain a composition (A2), at least comprising
   the at least one cyclic compound with Z cycles and 7 to 16 carbon atoms with a keto group,
   at least one cyclic compound with Z cycles and 7 to 16 carbon atoms with at least two keto groups and
   at least one compound with Z−1 cycles and 7 to 16 carbon atoms with at least one aldehyde group, and (b) distillative treatment of the composition (A2) from step (a2) in order to obtain a composition (B), comprising
   the at least one cyclic compound with Z cycles and 7 to 16 carbon atoms with a keto group,
   less than 0.3% by weight of the at least one cyclic compound with Z cycles and 7 to 16 carbon atoms with at least two keto groups and
   less than 1.0% by weight of the at least one compound with Z−1 cycles and 7 to 16 carbon atoms with at least one aldehyde group.

Besides the specified desired products, specified by-products and unreacted starting material, the composition (A1) usually comprises further compounds, in particular organic compounds, for example organic compounds with oxygen-containing groups, for example alcohols, aldehydes or epoxides. In this connection, the organic compounds can in particular have the same number of carbon atoms as, or a different number of carbon atoms than, the cyclic ketone present in the composition (A1). In addition to the specified components, unreacted dinitrogen monoxide and formed nitrogen may additionally be present in the composition (A1). Consequently, in a particularly preferred embodiment, stage (a1) comprises (a1) oxidation of a composition (A), at least comprising one cyclic olefin with Z cycles and 7 to 16 carbon atoms and at least two C—C double bonds, by means of dinitrogen monoxide to give a composition (A1), at least comprising
   the at least one cyclic compound with Z cycles and 7 to 16 carbon atoms with a keto group,
   at least one cyclic compound with Z cycles and 7 to 16 carbon atoms with at least two keto groups,
   the at least one cyclic olefin with Z cycles and 7 to 16 carbon atoms with at least two C—C double bonds and
   dinitrogen monoxide and nitrogen.

Within the context of the present invention, in stage (a1) dinitrogen monoxide can be used in pure form or in the form of a gas mixture comprising dinitrogen monoxide.

In principle, in stage (a1) of the process according to the invention it is possible to use any gas mixture comprising dinitrogen monoxide. According to the invention, it is also possible to purify or concentrate the gas mixture comprising dinitrogen monoxide prior to use in stage (a). A suitable purification process comprises, for example, the absorption of the gas mixture in an organic solvent or water, the desorption of the gas mixture from the laden organic solvent or the laden water and the adjustment of the content of nitrogen oxides $NO_x$ in the gas mixture to at most 0.01 to 0.001% by volume, based on the total volume of the gas mixture. Such a process is described, for example, in DE 10 2004 046 167.8, the content of which in this regard is incorporated in its entirety into the context of the present application.

Here, the gas mixture used comprising dinitrogen monoxide can in principle originate from any desired source. In particular, it is possible for the dinitrogen monoxide source used to be the off-gas of a process as described in WO 2006/032502, WO 2007/060160 and WO 2008/071632, and in the as yet unpublished applications EP 08153953.8 and EP 08153952.0.

The term "gas mixture" as used within the context of the present invention refers to a mixture of two or more compounds which are in the gaseous state at ambient pressure and ambient temperature. If the temperature is changed or the pressure is changed, the gas mixture may also be present in another state, for example liquid, and is still referred to as a gas mixture within the context of the present invention.

According to the invention, a mixture of different off-gases can also be used.

According to a further preferred embodiment of the present invention, the at least one off-gas comprising dinitrogen monoxide originates from an adipic acid plant, a dodecanedioic acid plant, a hydroxylamine plant and/or a nitric acid plant, the latter in turn preferably being operated with at least one offgas from an adipic acid plant, a dodecanedioic acid plant, a glyoxal plant or a hydroxylamine plant.

According to the invention, the gas mixture can be used in gaseous form. However, it is also possible to firstly treat the gas mixture comprising dinitrogen monoxide in such a way that the gas mixture and/or dinitrogen monoxide is present in liquid or supercritical form and is then used. The gas mixture and/or dinitrogen monoxide can be liquefied through appropriate selection of the pressure or the temperature. Within the context of the present invention, it is likewise possible to dissolve the gas mixture in a solvent.

The reaction of the at least one cyclic olefin with Z cycles and 7 to 16 carbon atoms and at least two C—C double bonds with dinitrogen monoxide according to step (a1) can in principle take place in the presence of a catalyst, but also without the addition of a catalyst.

After stage (a1), the composition (A1) obtained in stage (a1) is treated in stage (a2) according to the invention.

In a preferred embodiment, the composition (A1) obtained from stage (a1) is decompressed in a stage (a1b) in order to remove any gaseous starting materials or products that are still present, for example unreacted $N_2O$ or $N_2$ which has formed, before composition (A1) is used in stage (a2). The decompression can take place by processes known to the person skilled in the art, for example by transferring the composition (A1) to a room in which a lower pressure prevails.

Consequently, the process according to the invention preferably comprises a step (a1b)

(a1b) decompression of the composition (A1) in order to remove dinitrogen monoxide and nitrogen in order to obtain a composition (A1) which is essentially free from dinitrogen monoxide and nitrogen.

Stage (a2):

(a2) separating off the at least one cyclic olefin with Z cycles and 7 to 16 carbon atoms with at least two C—C double bonds from the composition (A1) from stage (a1) in order to obtain a composition (A2), at least comprising the at least one cyclic compound with Z cycles and 7 to 16 carbon atoms with a keto group and at least one compound with Z−1 cycles and 7 to 16 carbon atoms with at least one aldehyde group.

In stage (a2) of the process according to the invention, starting material of the process according to the invention which has not been reacted in the oxidation reaction in stage (a1) is separated off from the composition (a1) in order to obtain the composition (A2).

Stage (a2) can take place by all methods known to the person skilled in the art. In one preferred embodiment, in stage (a2) of the process according to the invention, a distillation is carried out in order, for example, to separate off unreacted starting material, i.e. at least one cyclic olefin with Z cycles and 7 to 16 carbon atoms with at least two C—C double bonds, from the product stream in order preferably to return it to stage (a1) of the process according to the invention.

In one preferred embodiment, a simple distillation column with packing known to the person skilled in the art is used for the distillation in stage (a2). The distillation in stage (a2) of the process according to the invention is preferably carried out in vacuo, for example at a pressure of ≦1000 mbar, preferably ≦500 mbar, particularly preferably 5, 300 mbar. For the case preferred according to the invention where the starting material used is an olefinic compound with 12 carbon atoms, stage (a2) is carried out preferably at a pressure of ≦120 mbar, particularly preferably ≦70 mbar, very particularly preferably ≦60 mbar. According to the invention, distillation columns known to the person skilled in the art can be used, preference being given to those which have at least 20, preferably at least 25, particularly preferably at least 30, theoretical plates. In a further preferred embodiment, 35 to 55% of the plates are located in the stripping section of the distillation column. In the preferred embodiment where an olefinic compound with 12 carbon atoms is used as starting material, the reflux ratio is 1 to 2, preferably 1.2 to 1.8. For the other specified starting materials, the reflux ratio can be adjusted by the person skilled in the art.

The top product obtained from this distillation is essentially pure starting material, i.e. at least one cyclic olefin with Z cycles and 7 to 16 carbon atoms with at least two C—C double bonds, which, in a particularly preferred embodiment, is returned as substrate to stage (a1) of the process according to the invention.

The bottom product obtained in stage (a2) in the described distillation essentially corresponds to the above described composition (A2).

In the preferred embodiment of the process according to the invention where the composition (A1) also comprises at least one cyclic compound with Z cycles and 7 to 16 carbon atoms and at least two keto groups, in stage (a2) of the process according to the invention, a composition (A2) is obtained, at least comprising the at least one cyclic compound with Z cycles and 7 to 16 carbon atoms with a keto group, at least one cyclic compound with Z cycles and 7 to 16 carbon atoms with at least two keto groups and at least one compound with Z−1 cycles and 7 to 16 carbon atoms with at least one aldehyde group.

Step (b):

Step (b) of the process according to the invention comprises the (b) distillative treatment of the composition (A2) from step (a2) in order to obtain a composition (B), comprising the at least one cyclic compound with Z cycles and 7 to 16 carbon atoms with a keto group and less than 1.0% by weight of the at least one compound with Z−1 cycles and 7 to 16 carbon atoms with at least one aldehyde group.

In the preferred embodiment of the process according to the invention where the composition (A1) also comprises at least one cyclic compound with Z cycles and 7 to 16 carbon atoms and at least two keto groups, in stage (b) of the process according to the invention, a composition (B) is obtained, at least comprising the at least one cyclic compound with Z cycles and 7 to 16 carbon atoms with a keto group, less than 0.5% by weight of the at least one cyclic compound with Z cycles and 7 to 16 carbon atoms with at least two keto groups and less than 1.0% by weight of the at least one compound with Z−1 cycles and 7 to 16 carbon atoms with at least one aldehyde group.

The quantitative data refer in each case to the total composition (B). The present invention consists inter alia in treating the composition (A2) from step (a2) by distillation in order to obtain the compositions (B) described above.

In this connection, it is essential to the invention that the composition (B) comprises less than 1.0% by weight, preferably less than 0.5% by weight, particularly preferably less than 0.2% by weight, of the at least one compound with Z−1 cycles and 7 to 16 carbon atoms with at least one aldehyde group, in particular the specified dodecatrienal isomers, in each case based on the total composition (B).

In a particularly preferred embodiment, the composition (B) comprises less than 0.5% by weight, preferably less than 0.3% by weight, particularly preferably less than 0.25% by weight, of the at least one cyclic compound with Z cycles and 7 to 16 carbon atoms with at least two keto groups, in particular the specified cyclododecenedione isomers, and less than 1.0% by weight, preferably less than 0.5% by weight, particularly preferably less than 0.2% by weight, of the at least one compound with Z−1 cycles and 7 to 16 carbon atoms with at least one aldehyde group, in particular the specified dodecatrienal isomers, in each case based on the total composition (B).

It is thus essential to the invention that the at least one compound with Z−1 cycles and 7 to 16 carbon atoms with at least one aldehyde group is depleted in stage (b) of the process according to the invention to a particularly low aforementioned amount. In one particularly preferred embodiment of the process according to the invention, both the at least one cyclic compound with Z cycles and 7 to 16 carbon atoms with at least two keto groups and the at least one compound with Z−1 cycles and 7 to 16 carbon atoms with at least one aldehyde group are in each case depleted to particularly low aforementioned amounts.

In one preferred embodiment, stage (b) of the process according to the invention is carried out in at least two columns. In one particularly preferred embodiment, composition (A2) from step (a2) is treated in a first step in a simple distillation column (T1). This gives preferably a top stream (K1), which consists essentially of at least one compound with Z−1 cycles and 7 to 16 carbon atoms with at least one aldehyde group, and, if appropriate, at most 35% by weight, preferably at most 30% by weight, particularly preferably at most 25% by weight, of at least one cyclic compound with Z cycles and 7 to 16 carbon atoms with at least two keto groups. Furthermore, a bottom stream (S1) is obtained which can comprise all residual components.

As distillation column (T1) it is possible to use all columns known to be suitable to the person skilled in the art. In one preferred embodiment, the column (T1) comprises at least 10 theoretical plates, particularly preferably at least 15 theoretical plates, very particularly preferably at least 20 theoretical plates. In this connection, it is further preferred that most of the plates, for example at least 50% of the plates, are in the rectifying section of the column. The distillation in the distillation column (T1) is preferably carried out at a pressure below atmospheric pressure, for example, particularly for the preferred case where the starting material used is an olefinic compound with 12 carbon atoms, at a top pressure of less than 50 mbar, particularly preferably less than 25 mbar. For the other compounds which can be used according to the invention, a suitable pressure can be ascertained by the person skilled in the art. The distillation in the distillation column (T1) is carried out for the preferred case where the starting material used is an olefinic compound with 12 carbon atoms preferably at a bottom temperature of from 120 to 220° C., particularly preferably 150 to 200° C. For the other starting materials suitable according to the invention, the distillation temperature, also depending on the established pressure, can be selected by the person skilled in the art.

In a further preferred embodiment of step (b) of the process according to the invention, the bottom stream (S1) from the first distillation column (T1) is treated in at least one further simple distillation column (T2). In one preferred embodiment in this connection, a top stream (K2) is obtained which comprises essentially at least one cyclic compound with Z cycles and 7 to 16 carbon atoms with at least one keto group. In one, preferred embodiment, this top stream (K2) comprises essentially no compound with Z−1 cycles and 7 to 16 carbon atoms with at least one aldehyde group, i.e. less than 1.0% by weight, in a preferred embodiment at most 0.2% by weight. In the second distillation in T2 of the process according to the invention (step (b)), a bottom stream (S2) is furthermore obtained which comprises at least one cyclic compound with Z cycles and 7 to 16 carbon atoms with at least two keto groups and other by-products of the oxidation according to step (a1), but comprises at most 40% by weight, preferably at most 25% by weight, of the at least one cyclic compound with Z cycles and 7 to 16 carbon atoms with a keto group.

As distillation column (T2) it is possible to use any column which is known to be suitable to the person skilled in the art. In one preferred embodiment, the column has at least 30 plates, particularly preferably at least 35 plates. In a further preferred embodiment, most of the plates are in the stripping section, particularly preferably at least 28 theoretical plates are in the stripping section. The distillation in separating column (T2) preferably takes place at a pressure below atmospheric pressure, for the preferred case where an olefinic compound with 12 carbon atoms is used as starting material, for example at a top pressure of ≦50 mbar, particularly preferably ≦25 mbar. The distillation in the distillation column (T2) is carried out, for the preferred case where an olefinic compound with 12 carbon atoms is used, preferably at a bottom temperature of from 120 to 220° C., particularly preferably 150 to 200° C. For the other starting materials suitable according to the invention, the temperature, also depending on the established pressure, can be easily adjusted by the person skilled in the art.

According to the invention, it is also possible to operate the distillation columns (T1) and (T2) in reverse order, i.e. to separate in the first column the at least one cyclic compound with Z cycles and 7 to 16 carbon atoms with at least one keto group and the at least one compound with Z−1 cycles and 7 to 16 carbon atoms with at least one aldehyde group at the top, and in the second column to separate the purified at least one cyclic compound with Z cycles and 7 to 16 carbon atoms with at least one keto group at the bottom.

Very particularly preferably, instead of the two distillation columns (T1) and (T2) in step (b) of the process according to the invention, a single dividing wall column is used.

According to the invention, any dividing wall column which appears to be suitable to the person skilled in the art for the present separation problem can be used in step (b) of the process according to the invention.

In one preferred embodiment, a continuous dividing wall column is used, which preferably has at least three zones. The dividing wall column preferably has a lower zone, which has preferably at least 2, particularly preferably at least 4, theoretical trays. Furthermore, the preferably used dividing wall column has a middle section, which preferably has at least 15, particularly preferably at least 25, theoretical trays. In a further preferred embodiment, the dividing wall column used has an upper section, which preferably has at least 4, particularly preferably at least 7, theoretical trays. The middle section is subdivided into an inlet section and an outlet section by a dividing wall which is preferably arranged in the middle.

In a further preferred embodiment, the dividing wall column is equipped with a suitable packing. Suitable column packings are known to the person skilled in the art, for example from J. F. Fair in "Handbook of Separation Process Technology", R. W. Rousseau (Ed), (1987), John Wiley & Sons, pages 295-312.

In order to be able to keep the temperature during the distillation in the dividing wall column as low as possible, a pressure below atmospheric pressure is preferably used, for example a pressure within the dividing wall column of less than 500 mbar, preferably less than 200 mbar, in particular less than 100 mbar and very particularly preferably less than 50 mbar. The pressure difference between column bottom and column top is preferably less than 50 mbar, particularly preferably less than 30 mbar.

In the dividing wall column, the distillation is carried out preferably at a bottom temperature of from 150 to 220° C., particularly preferably 160 to 200'C. The temperature at the side takeoff at which preferably composition (B) is removed is preferably 110 to 180° C., particularly preferably 130 to 170° C. The top temperature in the dividing wall column is preferably 80 to 150° C., particularly preferably 100 to 135° C. These values apply in particular for the preferred case where an olefinic compound with 12 carbon atoms is used as starting material; for the other starting materials which can be used according to the invention, the values can be adjusted accordingly by the person skilled in the art.

Low-boiling components of the composition (A2) are preferably separated off as top stream (K3) at the top of the dividing wall column. In one preferred embodiment, top stream (K3) comprises at least 30% by weight, particularly preferably at least 50% by weight, very particularly preferably at least 70% by weight, of at least one compound with Z−1 cycles and 7 to 16 carbon atoms and at least one aldehyde group.

High-boiling components of the composition (A2) are preferably separated off as bottom stream (S2) at the bottom of the dividing wall column. In one preferred embodiment, bottom stream (S2) comprises at least one cyclic compound with Z cycles and 7 to 16 carbon atoms with at least two keto groups and other by-products of the oxidation according to step (a1), but comprises at most 40% by weight, preferably at most 25% by weight, of the at least one cyclic compound with Z cycles and 7 to 16 carbon atoms with a keto group.

Composition (B) is obtained via the side takeoff of the dividing wall column.

Following the distillative treatment according to step (b) of the process according to the invention, a composition (B) is obtained which essentially comprises the desired product, the at least one cyclic compound with Z cycles and 7 to 16 carbon atoms with a keto group.

Furthermore, at least one cyclic compound with Z cycles and 7 to 16 carbon atoms with at least two keto groups and at least one compound with Z–1 cycles 7 to 16 carbon atoms with at least one aldehyde group are present in the composition (B) according to the invention, if appropriate as by-products, in the small amounts stated above.

The advantages of the process according to the invention, in particular of step (b), are that, through the distillative treatment of the composition (A2), a composition (B) is obtained which has a very low content of at least one compound with Z–1 cycles and 7 to 16 carbon atoms with at least one aldehyde group. If this by-product of the oxidation according to stage (a1) is present in higher amounts than possible through the process according to the invention, then, as is customary in the processes of the prior art, the following disadvantages arise in the further course of the process.

If the at least one compound with Z–1 cycles and 7 to 16 carbon atoms and at least one aldehyde group is not separated off by stage (b) according to the invention, then, as a result of a hydrogenation, which is carried out if appropriate, the corresponding compounds carrying saturated aldehyde groups and/or hydroxy groups are thus formed, particularly preferably, for example, dodecanal and/or dodecanol. In the preferred case where the desired main product is cyclododecanone, these by-products can only be separated off with difficulty by customary processes, meaning that it is not possible to obtain a highly pure product.

In the case preferred according to the invention where, in the oxidation according to step (a1) of the process according to the invention, besides the desired product, inter alia also at least one cyclic compound with Z cycles and 7 to 16 carbon atoms with at least two keto groups is formed, the following secondary reactions can moreover take place.

Under the influence of a base, the specified diketones very readily enter into an intramolecular aldol reaction. Thus, under basic conditions, for example cis-cyclododec-8-ene-1,5-dione (XII), which with ca. 38% may be the main isomer among the diketones preferably formed in step (a1) of the process according to the invention, converts to (Z)-3,4,5,6,7,10-hexahydro-2H-benzocycloocten-1-one (XIV). During a subsequent hydrogenation, which is carried out if appropriate, this is converted to decahydrobenzocycloocten-1-one (XV).

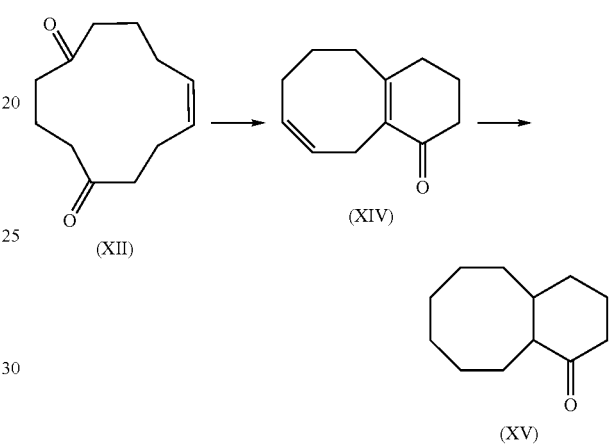

Decahydrobenzocycloocten-1-one (XV) and similar bicyclic $C_{12}$ ketones which are formed from the other cyclododecenediones have boiling points which are close to the boiling point of cyclododecanone, meaning that during a final distillative purification it is difficult or impossible to obtain this desired product in the desired high purity. The other starting materials which can be used according to the invention also lead to corresponding by-products which can be separated off by distillation only with difficulty.

For example, when using cycloocta-1,5-diene (I), the following by-products are obtained:

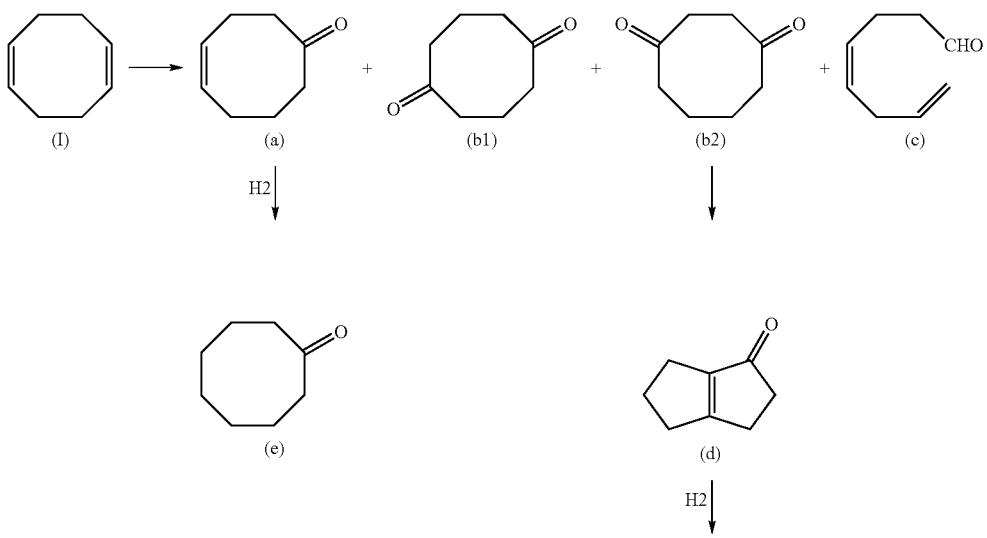

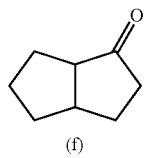

(f)

In this specific embodiment of the process according to the invention, in the oxidation with N₂O, a mixture of the desired unsaturated monoketone (a), of the two diketones (b1) and (b2), which correspond to the at least one cyclic compound with Z cycles and 7 to 16 carbon atoms and two keto groups, and of the aldehyde (c), which corresponds to the at least one compound with Z–1 cycles and 7 to 16 carbon atoms with an aldehyde group is formed. The ketone (b2) enters very readily into an intramolecular aldol condensation (sometimes even merely by heating) with the formation of (d). If the diketones are not separated off, preferably by step (b) according to the invention, (d) is formed, which is then hydrogenated to (f). The boiling points of (e), which following hydrogenation is the desired product of the overall process, and (f), however, are very similar (e: 74° C. and f: 72° C. in each case at 12 Torr), which makes the purification of (e) extremely difficult.

The processes known from the prior art in which the reaction mixtures comprising diketones obtained from the oxidation reaction are firstly hydrogenated have a similar disadvantage. As a result of hydrogenation, the unsaturated diketones, for example the aforementioned cyclodecenediones (XII), produce the corresponding saturated compounds, for example cyclododecanediones, in particular cyclododecane-1,5-dione (XVI). Under the conditions of a thermal treatment, which is carried out if appropriate, in the presence of a catalyst of the reaction mixture, for example as described in WO 2008/000754, for example cyclododecane-1,5-dione (XVI), which with 50% constitutes the main isomer among the formed cyclododecanediones, is converted to 3,4,5,6,7,8,9,10-octahydro-(2H)-benzocycloocten-1-one (XVII).

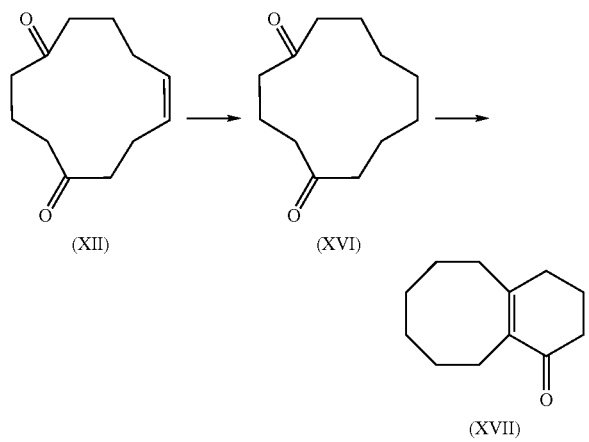

Compound (XVII) has a boiling point which is likewise very close to that of the preferably desired product of value cyclododecanone, meaning that distillative separation is difficult or impossible.

Through step (b) of the process according to the invention, it is possible to separate off the specified by-products of the oxidation, for example unsaturated aldehydes and if appropriate diketones, from the reaction mixture so thoroughly that the described undesired secondary reactions cannot take place or can take place only to a slight degree, meaning that the compounds which cannot be separated off or are difficult to separate off cannot be formed or can only be formed in small amounts.

Stage c):

In a further preferred embodiment of the process according to the invention, stage (b) is followed by at least the following stage (c):

(c) hydrogenation of the composition (B) in the presence of at least one catalyst in order to obtain a composition (C).

Irrespective of which regio isomer of the at least one cyclic compound with Z cycles and 7 to 16 carbon atoms with a keto group, for example cyclododecadienone, or which mixture of at least two regio isomeric cyclic compounds with Z cycles and 7 to 16 carbon atoms with a keto group is obtained from the reaction according to the invention with dinitrogen monoxide according to step (a) and from the distillative treatment according to step (b), these compounds without exception comprise at least one remaining, i.e. nonoxidized, double bond, which is hydrogenated in optional step (c) of the process according to the invention in order to obtain a composition (C) comprising at least one saturated cyclic compound with Z cycles and 7 to 16 carbon atoms and a keto group.

According to a particularly preferred embodiment of stage (c) of the process according to the invention, cyclododeca-4,8-dienone is hydrogenated to cyclododecanone. Accordingly, the present invention also relates to a process as described above where the cyclododecadienone obtained from the reaction of cyclododecatriene with dinitrogen monoxide according to step (a1), the treatment according to step (a2) and the distillative treatment according to step (b) is hydrogenated in step (c) to give cyclododecanone.

All suitable catalysts can be used for the hydrogenation of composition (B), particularly preferably of cyclododeca-4,8-dienone. In particular, at least one homogeneous or at least one heterogeneous or both at least one homogeneous and at least one heterogeneous catalyst can be used.

Preferably, the catalysts which can be used comprise at least one metal from the 7th, 8th, 9th, 10th or 11th subgroup of the periodic table of the elements. Further preferably, the catalysts which can be used according to the invention in optional step (C) comprise at least one element selected from the group consisting of Re, Fe, Ru, Co, Rh, Ir, Ni, Pd, Pt, Cu and Au. Particularly preferably, the catalysts which can be used according to the invention comprise at least one element selected from the group consisting of Fe, Ni, Pd, Pt and Cu. Particularly preferably, the catalysts used according to the invention comprise Pd.

In optional step (c) of the process according to the invention, preferably used homogeneous catalysts comprise at least one element of the 8th, 9th or 10th subgroup. Further preference is given to homogeneous catalysts which comprise Ru, Rh, Ir and/or Ni. For example, in this connection for example RhCl(TTP)₃ or Ru₄H₄(CO)₁₂ are to be mentioned. Particular preference is given to those homogeneous catalysts which comprise Ru. For example, homogeneous catalysts are used as are described in U.S. Pat. No. 5,180,870, U.S. Pat. No. 5,321,176, U.S. Pat. No. 5,177,278, U.S. Pat. No. 3,804,914, U.S. Pat. No. 5,210,349, U.S. Pat. No. 5,128,296, U.S. Pat. No. 316,917 and in D. R. Fahey in J. Org. Chem. 38 (1973) pp. 80-87, the disclosure of which in this regard is incorporated in its entirety into the context of the present application. Such catalysts are, for example, $(TPP)_2(CO)_3Ru$, $[RU(CO)_4]_3$, $(TPP)_2Ru(CO)_2Cl_2$, $(TPP)_3(CO)RuH_2$, $(TPP)_2(CO)_2RuH_2$, $(TPP)_2(CO)_2RuClH$ or $(TPP)_3(CO)RuCl$.

Particularly preferably, in optional step (c) of the process according to the invention, at least one heterogeneous catalyst is used, where at least one of the aforementioned metals can be used as metal as such, as Raney catalyst and/or applied to a customary support. Preferred support materials are, for example, activated carbons or oxides, such as, for example, aluminum oxides, silicon oxides, titanium oxides or zirconium oxides. Inter alia, bentonites are likewise to be mentioned as support materials. If two or more metals are used, then these can be present separately or as an alloy. In this connection, it is possible to use at least one metal as such and at least one other metal as Raney catalyst or at least one metal as such and at least one other metal, applied to at least one support, or at least one metal as Raney catalyst and at least one other metal, applied to at least one support, or at least one metal as such and at least one other metal as Raney catalyst and at least one other metal, applied to at least one support.

The catalysts used in optional step (c) of the process according to the invention may, for example, also be so-called precipitated catalysts. Such catalysts can be prepared by precipitating their catalytically active components from their salt solutions, in particular from the solutions of their nitrates and/or acetates, for example by adding solutions of alkali metal and/or alkaline earth metal hydroxide and/or carbonate solutions, for example sparingly soluble hydroxides, oxide hydrates, basic salts or carbonates, then drying the resulting precipitates and then converting these by calcination at generally 300 to 700° C., in particular 400 to 600° C., to the corresponding oxides, mixed oxides and/or mixed-valency oxides which are reduced and converted to the actual catalytically active form by a treatment with hydrogen or gases comprising hydrogen in the range from in general 50 to 700° C., in particular 100 to 400° C., to the relevant metals and/or oxidic compounds of lower oxidation state. Here, reduction is generally carried out until water is no longer formed. During the production of precipitated catalysts which comprise a support material, the precipitation of the catalytically active components can take place in the presence of the relevant support material. The catalytically active components can advantageously be precipitated at the same time as the support material from the relevant salt solutions.

Preferably, in optional step (c) of the process according to the invention, hydrogenation catalysts are used which comprise the metals or metal compounds catalyzing the hydrogenation deposited on a support material.

Apart from the aforementioned precipitated catalysts, which, apart from the catalytically active components, also additionally comprise a support material, of suitability for the process according to the invention are in general those support materials in which the catalytically hydrogenating component have been applied to a support material, for example, by impregnation.

The manner in which the catalytically active metal is applied to the support is generally not critical and can be effected in a variety of ways. The catalytically active metals can be applied to these support materials for example by impregnation with solutions or suspensions of the salts or oxides of the relevant elements, drying and subsequent reduction of the metal compounds to the relevant metals or compounds of lower oxidation state by means of a reducing agent, preferably with hydrogen or complex hydrides. Another option of applying the catalytically active metals to these supports is to impregnate the supports with solutions of thermally readily decomposable salts, for example with nitrates or thermally readily decomposable complex compounds, for example carbonyl or hydrido complexes of the catalytically active metals, and to heat the support impregnated in this way to temperatures in the range from 300 to 600° C. to thermally decompose the adsorbed metal compounds. This thermal decomposition is preferably carried out under a protective gas atmosphere. Suitable protective gases are, for example, nitrogen, carbon dioxide, hydrogen or the inert gases. Furthermore, the catalytically active metals can be deposited on the catalyst support by evaporative coating or by flame spraying. The content of the catalytically active metals in these support catalysts is in principle not critical for the success of the process according to the invention. In general, relatively high contents of catalytically active metals in these support catalysts lead to higher space-time conversions than lower contents. In general, support catalysts are used whose content of catalytically active metals is in the range from 0.1 to 90% by weight, preferably in the range from 0.5 to 40% by weight: based on the total weight of the catalyst. Since this content data refers to the entire catalyst including support material, although the different support materials have very different specific weights and specific surface areas, it is also conceivable that this data may also not be reached or may be exceeded without adversely affecting the result of the process according to the invention. A plurality of the catalytically active metals can of course also be applied to the respective support material. Furthermore, the catalytically active metals can, for example, be applied to the support in accordance with the process of DE-OS 25 19 817 or EP 0 285 420 AI.

Both the activation of the precipitated catalysts and also of the support catalysts can also take place in situ at the start of the reaction due to the hydrogen which is present. Preferably, these catalysts are activated separately prior to their use.

Support materials which can be used are in general the oxides of aluminum and titanium, zirconium dioxide, silicon dioxide, clay earths such as, for example, montmorillonites, silicates, such as, for example, magnesium or aluminum silicates, zeolites, such as, for example, the structure types ZSM-5 or ZSM-10, or activated carbon. Preferred support materials are aluminum oxides, titanium dioxides, silicon dioxide, zirconium dioxide and activated carbon. Mixtures of different support materials can of course also serve as support for catalysts which can be used in optional step (c) of the process according to the invention.

The at least one heterogeneous catalyst can be used in optional step (c) of the process according to the invention for example as suspension catalyst and/or as fixed bed catalyst.

If, for example, in the course of the process according to the invention, the optional hydrogenation according to step (c) is carried out with at least one suspension catalyst, then the hydrogenation is preferably carried out in at least one stirred reactor, or in at least one bubble column or in at least one packed bubble column or in a combination of two or more identical or different reactors.

In the present case, the term "different reactors" refers both to different reactor types and also reactors of the same type which differ, for example, by virtue of their geometry, such as, for example, their volume and/or their cross section and/or by virtue of the hydrogenation conditions in the reactors.

If, for example, in the course of optional step (c) of the process according to the invention, the hydrogenation is carried out with at least one fixed-bed catalyst, then preferably at least one tubular reactor, such as, for example, at least one shaft reactor and/or at least one tube-bundle reactor, is used, where an individual reactor can be operated in upward or downward flow mode. When using two or more reactors, at least one can be operated in upward flow mode and at least one can be operated in downward flow mode.

According to a preferred embodiment of optional step (c) of the process according to the invention, the at least one catalyst used for the hydrogenation is separated off from the product mixture of the hydrogenation. This separation can take place according to any suitable procedure depending on the catalyst used.

If the catalyst used during the hydrogenation is, for example, a heterogeneous catalyst as suspension catalyst, then in the course of the present invention this is preferably separated off by at least one filtration step. The catalyst separated off in this way can be returned to the hydrogenation or be fed to at least any one other process. It is likewise possible to work up the catalyst in order, for example, to recover the metal present in the catalyst.

If the catalyst used in the hydrogenation is, for example, a homogeneous catalyst, then in the course of the present invention, this is preferably separated off by at least one distillation step. In the course of this distillation, one or two or more distillation columns can be used. The catalyst separated off in this way can be returned to the hydrogenation or be fed to at least any one other process. It is likewise possible to work up the catalyst in order, for example, to recover the metal present in the catalyst.

Prior to use in a process as desired, such as, for example, before being returned to the process according to the invention, both the at least one homogeneous and also the at least one heterogeneous catalyst can, should this be required, be regenerated by at least one suitable process.

In the case of the reactor used according to the invention, the heat can be dissipated internally, for example via cooling coils, and/or externally, for example via at least one heat exchanger. If, for example, preferably at least one tubular reactor is used for the hydrogenation, then the reaction is preferably run via an external circuit in which the heat dissipation is integrated.

If, according to a preferred embodiment of the process according to the invention, the hydrogenation is carried out continuously; further preferably at least two reactors, further preferably at least two tubular reactors, further preferably at least two serially coupled tubular reactors and especially preferably two serially coupled tubular reactors, are used. The hydrogenation conditions in the reactors used can in each case be identical or different and are in each case within the ranges described above.

If the hydrogenation is carried out over at least one suspended catalyst, the residence time is generally in the range from 0.5 to 50 h, preferably in the range from 1 to 30 h and particularly preferably in the range from 1.5 to 25 h. Here, it is unimportant whether one reactor or at least 2 serially connected reactors are used according to the invention. For all of these embodiments, the total residence time is within the ranges stated above.

If, in the course of the process according to the invention, the hydrogenation is carried out in continuous mode over at least one fixedly arranged catalyst, then the residence time is generally in the range from 0.1 to 20 h, preferably in the range from 0.2 to 15 h and particularly preferably in the range from 0.3 to 10 h. In this connection, it is unimportant whether one reactor or at least 2 serially connected reactors are used according to the invention. For all of these embodiments, the total residence time is within the ranges stated above.

The mixture which is obtained from the first tubular reactor comprises the desired product, for example cyclododecanone, in a fraction preferably in the range from 50 to 99.9% by weight and particularly preferably in the range from 70 to 99.5% by weight. This mixture, if appropriate after at least one suitable interim treatment, is fed to the second tubular reactor. The mixture which is obtained from the second tubular reactor comprises cyclododecanone in a fraction preferably in the region of at least 99.5%, further preferably in the region of 99.9% and in particular 99.99% by weight, particularly preferably in the region of at least 99.9% and especially preferably at least 99.99% by weight.

The hydrogen pressure during the hydrogenation according to the invention in optional step (c) is generally in the range from 1 to 325 bar, preferably in the range from 1.5 to 200 bar, further preferably in the range from 2 to 100 bar and especially preferably in the range from 2.5 to 50 bar.

The hydrogenation temperature is generally in the range from 0 to 250° C., preferably in the range from 20 to 200° C., for example in the range from 30 to 180° C., further preferably in the range from 30 to 150° C., particularly preferably in the range from 40 to 170° C. and especially preferably in the range from 40 to 140° C.

Accordingly, the present invention also relates to a process as described above wherein the hydrogenation in step (c) is carried out in the presence of a hydrogenation catalyst, preferably a heterogeneous hydrogenation catalyst, at a temperature in the range from 0 to 250° C. and a pressure in the range from 1 to 325 bar.

In the course of the hydrogenation according to the invention, at least one suitable solvent or diluent can be used. Ones to be mentioned are, inter alia, cyclododecanone or cyclododecane and fundamentally all solvents and diluents which are not hydrogenated or converted in some other way under the hydrogenation conditions.

According to one preferred embodiment of the process according to the invention, the hydrogenation is carried out without the addition of a solvent or diluent.

The hydrogenation according to the invention generally produces a mixture which, besides the at least one cyclic compound with Z cycles and 7 to 16 carbon atoms and a keto group, in particular cyclododecanone, has the aforementioned by-products in the specified very small amounts.

The process according to the invention for preparing at least one cyclic compound with Z cycles and 7 to 16 carbon atoms with a keto group, for example cyclododecanone, offers inter alia the advantage that this ketone are obtained in few steps and at the same time with high selectivity. A further considerable advantage is the fact that a starting material which can be used for the process according to the invention is offgases comprising dinitrogen monoxide from preferably industrial plants which, on the one hand, are available without great expenditure, which on the other hand permit the integration of the process according to the invention into the existing plant assembly, as a result of which the transportation route for the starting material can be kept to a minimum, and which furthermore, being potential greenhouse gases, do not have to be passed to a particular treatment for disposal, but flow directly into a product of value.

The present invention also relates to the process according to the invention where stage (b) is followed by at least the following stage (d):

(d) treatment of the composition (B) from stage (b) with at least one base in order to obtain a composition (D).

According to the invention, the composition (B) is treated in the optional stage (d) with at least one base. Here, the process conditions of the treatment can be varied within wide ranges, provided it is ensured that the concentration of at least one troublesome secondary component, in particular at least one aldehyde, for example a compound with Z cycles and 7 to 16 carbon atoms with at least one aldehyde group, which can be formed in stage (a1) as by-product, is reduced.

According to the invention, in this connection, the amount of the at least one compound with Z–1 cycles and 7 to 16 carbon atoms with at least one aldehyde group is preferably further reduced. In this connection, according to the invention in accordance with step (b), if appropriate compounds with Z–1 cycles and 7 to 16 carbon atoms with at least one aldehyde group that are still present are preferably degraded to more than 90%, in particular to more than 95% and particularly preferably to 99.99%.

Compounds with Z cycles with 7 to 16 carbon atoms and at least one aldehyde group formed if appropriate in the oxidation in step (a1), i.e. cyclic aldehydes which are formed by ring contraction, are preferably degraded to up to 30%, in particular to up to 35% and particularly preferably to up to 40%. According to the invention, the at least one cyclic compound with Z cycles and 7 to 16 carbon atoms and a keto group is degraded only to 0.5 to 2.0%, preferably to 0.75 to 1.75%, in particular to 1.0 to 1.5%.

In a first approximation, one mole of product of value, i.e. compound with Z cycles and 7 to 16 carbon atoms and a keto group, is degraded per mole of compound with an aldehyde group.

According to the invention, the treatment with at least one base according to stage (d) preferably takes place for a period from 1 minute to 10 hours, in particular 5 minutes to 5 hours, particularly preferably 10 to 60 minutes, further preferably 20 to 50 minutes.

Here, the treatment can take place in the course of the process according to the invention in particular at a temperature of from 100 to 250° C., preferably 110 to 220° C., particularly preferably 120 to 200° C., further preferably 150 to 190° C.

The present invention according to a further embodiment consequently also relates to a process as described above for preparing a cyclic compound with Z cycles and 7 to 16 carbon atoms with a keto group, where the treatment according to stage (d) takes place at a temperature of from 100 to 250° C. and for a period of from 1 minute to 10 hours.

All possible reactor types are suitable for the treatment with the base. For a continuous reaction procedure, preference is given to using reactors with tubular characteristics, such as, for example, tubular reactors, cascades of stirred-tank reactors or comparable reactors. For a discontinuous reaction procedure (batch process), simple stirred-tank reactors are highly suitable. Preferably, the reaction proceeds essentially homogeneously in the liquid phase.

Preferably, the treatment according to stage (d) comprises two part steps (d1) and (d2), where according to step (d1) the composition (B) is treated with at least one base and according to step (d2) the base is separated off.

Consequently, according to a further embodiment, the present invention also relates to a process as described above for preparing a cyclic compound with Z cycles and 7 to 16 carbon atoms with a keto group, where stage (d) comprises the part steps (d1) and (d2):
(d1) treatment of the composition (B) with at least one base,
(d2) separating off the base.

The base can be separated off according to (d2) by all customary processes, for example by distillation. Particularly if NaOH or KOH are used as base, the removal takes place preferably by evaporation, for example in the form of a falling-film evaporator, a wiped film evaporator or helical tube evaporator, or by extraction of the base, for example with water.

Within the context of the present invention, all suitable bases can in principle be used. Preference is given to using organic or inorganic bases whose conjugated acid have a $pK_a$ in water of >9. Within the context of the present invention, preference is given, for example, to trialkylamines, alkali metal or alkaline earth metal alcoholates and tetraalkylammonium, alkali metal or alkaline earth metal hydroxides. Very particular preference is given to sodium hydroxide and potassium hydroxide.

According to the invention, the base can be used either as pure substance or as solution. Liquid bases are preferably used without the addition of a solvent. Solid bases are preferably used as solution. The solvent used is preferably the conjugated acid. The particularly preferred bases NaOH and KOH are preferably used as concentrated aqueous solution. Preferably, a base used as solution has a concentration of at least 25% by weight, in particular of at least 40% by weight, particularly preferably of about 50% by weight.

The amount of base used according to stage (d) can be varied within wide ranges. Between 0.01 and 5 mol of base/mole of aldehyde can be used. Preferably, between 0.05 and 2 mol of base/mole of aldehyde are used. Particular preference is given to using between 0.1 and 1 mol of base/mole of aldehyde in the mixture to be treated. At this point, aldehyde is to be understood as meaning the sum of all of the aldehydes present.

The treatment with the base is carried out in the temperature range between 100 and 250° C. Preferably, the reaction is carried out between 110 and 220° C. The reaction is particularly preferably carried out between 150 and 190° C. The duration of the treatment is determined by the selected temperature, type and amount of base and by the desired degree of depletion for the aldehydes. In this connection, the conditions are preferably selected such that the duration of the treatment is between 1 minute and 10 hours, for example between 10 minutes and 5 hours, preferably between 20 minutes and 2 hours, in particular between 30 minutes and 1.5 hours, particularly preferably between 40 minutes and 1 hour.

According to a preferred embodiment, the treatment with the base is carried out at a temperature of from 160 to 185° C. for a time from 30 to 40 minutes. Preferably, the treatment is carried out with 0.1 to 0.15% by weight of sodium hydroxide, based on the total composition. According to a particularly preferred embodiment, the treatment with the base is carried out at a temperature of from 160 to 185° C. for a time from 30 to 40 minutes with 0.1 to 0.15% by weight of sodium hydroxide, based on the total composition.

After optional step (d) of the process according to the invention, a composition (D) is obtained. This composition (D) preferably comprises at least 85% by weight of the cyclic compound with Z cycles and 7 to 16 carbon atoms and a keto group, particularly preferably at least 95% by weight of the cyclic compound with Z cycles and 7 to 16 carbon atoms and a keto group.

In a particularly preferred embodiment of the process according to the invention, step (d) of the process according to the invention is followed by a hydrogenation step (c').

The present invention therefore also relates to the process according to the invention where stage (d) is followed by at least the following stage (c'):
(c') hydrogenation of the composition (D) in the presence of at least one catalyst in order to obtain a composition (C').

This hydrogenation step is generally carried out analogously to optional step (c) described above. After optional step (c'), a composition (C') is obtained. In one preferred embodiment, this comprises at least 90% by weight of a saturated cyclic compound with Z cycles and 7 to 16 carbon atoms with a keto group, particularly preferably at least 95% by weight of a saturated cyclic compound with Z cycles and 7 to 16 carbon atoms with a keto group. As regards the processing parameters such as, for example, catalyst, pressure, temperature, quantitative amounts etc., that stated with regard to stage (c) applies for stage (c') according to the invention.

In a further preferred embodiment of the process according to the invention, hydrogenation step (c) or the optional hydrogenation step (c') is followed by the following step (e):

(e) purification of the composition (C) from step (c) or (C') from step (c'), at least comprising the steps (e1) thermal treatment of the composition (C) or (C') with at least one acid, or at least one catalyst which comprises at least one transition metal, (e2) further purification by a process selected from the group consisting of distillation, extraction and crystallization.

According to the invention, the composition (C) or (C') can be used directly in stage (e). However, it is also possible for composition (C) or (C') to be subjected to an interim treatment prior to stage (e). In one preferred embodiment, step (e) is carried out directly after step (c), meaning that steps (d) and (c') are not carried out.

The optional stage (e) of the process according to the invention comprises stages (e1) and (e2). According to stage (e1), the composition (C) or (C') is thermally treated with an acid or with a catalyst which comprises at least one transition metal.

The treatment with acid or with a catalyst which comprises at least one transition metal takes place preferably at temperatures of from 30 to 350° C., for example 60 to 350° C., in particular from 100 to 270° C., particularly preferably from 130 to 260° C.

Consequently, according to a further embodiment, the present invention also relates to a process as described above for preparing a cyclic compound with Z cycles and 7 to 16 carbon atoms and a keto group, where the treatment according to step (e1) is carried out at a temperature of from 60 to 350° C.

Surprisingly, it has been found that in the treatment of compositions comprising at least one cyclic compound with Z cycles and 7 to 16 carbon atoms with a keto group with acids or with a catalyst which comprises at least one transition metal, in a subsequent further purification, for example by distillation, extraction and/or by crystallization, it is possible to obtain cyclic ketones in high yields in purities of more than 99.5%. In this connection, the cyclic ketone is itself not attacked or is only attacked very insignificantly. According to the invention, the separated-off compounds are in particular alcohols, aldehydes and epoxides.

Based on the cyclic ketone present in the composition, according to the invention less than 10% of the ketone is lost, preferably less than 5%, in particular less than 3%. Here, the treatment according to stage (e1) can take place either in the gas phase or in the liquid phase. The pressure can be adjusted here within wide ranges. It can be, for example, between 0.001 and 300 bar, preferably between 0.01 and 200 bar, particularly preferably between 0.1 and 100 bar. According to the invention, preference is given to a pressure at which low-boiling components which form if appropriate can be removed from the system by distillation, i.e. at a pressure of from 0.25 to 70 bar, preferably 0.35 to 50 bar, particularly preferably 0.5 to 30 bar.

The treatment according to stage (e1) can take place discontinuously or continuously, with a continuous treatment being preferred. The residence times here are, for example, between 0.1 and 50 hours, preferably between 0.2 and 24 hours, for example between 0.5 and 15 hours, in particular between 1 hour and 19 hours, particularly preferably between 1.5 and 10 hours.

Consequently, according to a further embodiment, the present invention also relates to a process as described above for preparing a cyclic compound with Z cycles and 7 to 16 carbon atoms and a keto group, where the treatment according to step (e1) is carried out for a time from 0.1 to 50 hours.

The acids used according to the invention are Brønstedt or Lewis acids, it also being possible to use mixtures of two or more acids. The acids used may be homogeneously dissolved or heterogeneous. According to the invention, heterogeneous acids can be suspended or arranged in a fixed manner.

Consequently, according to a further embodiment, the present invention also relates to a process as described above where the acid is present in homogeneous or heterogeneous form.

The homogeneously soluble acids used according to the invention are, for example, mineral acids or organic acids. Examples are sulfuric acid, sulfonic acids, nitric acid, hydrochloric acid, phosphoric acid, phosphorous acid, perchloric acid, heteropolyacids, as are described, for example, in EP 0 158 229 B1, $C_1$ to $C_{30}$ carboxylic acids such as formic acid, acetic acid, propionic acid, benzoic acid or the like.

Preferred homogeneous acids are phosphoric acid, phosphorous acid, sulfuric acid, sulfonic acids and heteropolyacids, such as, for example, phosphotungstic acid. Particular preference is given to phosphoric acid and phosphotungstic acid.

The content of homogeneously soluble acid is generally between 0.01 and 10% by weight, based on the cyclic ketone. Preference is given to using a homogeneously soluble acid in an amount of from 0.05 to 5% by weight, particularly preferably 0.1 to 1% by weight.

According to one preferred embodiment of the present invention, a homogeneously soluble acid is used in an amount of from 0.1 to 1% by weight.

Preferably, following distillative removal of the at least one cyclic compound with Z cycles and 7 to 16 carbon atoms and a keto group cyclic ketone, the acid is at least partly returned to the treatment stage.

Heterogeneous acids suitable according to the invention are, for example, metal-oxidic solids which may have been treated according to the invention to increase their acidic strength, for example with mineral acids such as phosphoric acid or sulfuric acid. Preference is given to using oxides or mixed oxides of B, Al, Si, Sn, Ti, Cr, Zr, Fe and Zn, which can also comprise further constituents. For example, zirconium oxide, titanium oxide, aluminum oxide, silicon oxide and combinations thereof such as alumosilicates such as e.g. zeolites, are suitable. For example, sheet silicates or natural clay earths can be used. Organic-based heterogeneous acids, such as, for example, acid ion exchangers, can likewise be used.

If step (e1) of the process according to the invention is carried out discontinuously with heterogeneous acids, then usually 0.1 to 50% by weight of acid, based on the at least one cyclic compound with Z cycles and 7 to 16 carbon atoms and a keto group, is used. Preference is given to using a heterogeneous acid in an amount of from 0.5 to 20% by weight, particularly preferably from 1 to 10% by weight.

If step (e1) of the process according to the invention is carried out continuously with a heterogeneous acid, then preferably a space velocity, i.e. the space velocity of the heterogeneous acid, of from 0.01 to 10 kg of at least one cyclic compound with 7 to 16 carbon atoms and a keto group/liter of catalyst/h is established. In particular, a space velocity of from 0.05 to 2 kg of cyclic compound/liter of catalyst/h, particularly preferably 0.1 to 1 kg of cyclic compound/liter of catalyst/h is established.

The catalysts used according to the invention comprise at least one transition metal, it also being possible to use catalysts comprising two or more transition metals or mixtures of two or more catalysts comprising at least one transition metal. The catalysts used can be homogeneously dissolved or heterogeneous. According to the invention, heterogeneous catalysts can be suspended or arranged in a fixed manner. Consequently, according to a further embodiment, the present invention also relates to a process as described above where the catalyst which comprises at least one transition metal is present in homogeneous or heterogeneous form.

Within the context of the present invention, catalysts comprising at least one transition metal which may be used are all customary catalysts. In this connection, suitable transition metals are in principle all transition metals known to the person skilled in the art.

The homogeneously soluble catalysts used according to the invention are described, for example, in Houben-Weyl, Methoden der Organischen Chemie [Methods of Organic Chemistry], volume IV/1 c, pages 45 to 67, Thieme Verlag Stuttgart, 1980.

Preferred homogeneous catalysts comprise Ru, Rh and/or Pd as transition metal. Particular preference is given to Ru.

The content of homogeneously soluble catalyst is generally between 0.001 and 1% by weight, based on the cyclic compound. Preference is given to using a homogeneously soluble catalyst in an amount of from 0.005 to 0.5% by weight, particularly preferably 0.01 to 0.1% by weight.

According to one preferred embodiment of the present invention, a homogeneously soluble catalyst is used in an amount of from 0.01 to 0.1% by weight.

Preferably, following distillative removal of the at least one cyclic compound with Z cycles and 7 to 16 carbon atoms and a keto group, the catalyst is at least partially returned to the treatment stage (e1).

Heterogeneous catalysts suitable according to the invention are described, for example, in Houben-Weyl, Methoden der Organischen Chemie [Methods of Organic Chemistry], volume IV/1c, pp. 16 to 26, Thieme Verlag Stuttgart, 1980. They comprise at least one transition metal. Preferred transition metals are Ni, Cu, Pd, Ru, Ir, Pt, Co and/or Rh. Particular preference is given to Pd, Ru, Pt, very particular preference is given to Ru and Pd.

The heterogeneous catalysts can be used in suspended form or preferably arranged in a fixed manner. The catalysts comprising at least one transition metal can comprise the transition metal as element or in the form of a chemical compound, for example as oxide. Mixtures of different transition metals can comprise the elements or their compounds as mixtures or as alloys. Here, it is also possible to use non-transition-metal-containing elements or their compounds as catalyst component, for example in the so-called Raney catalysts, where, for example, Al or aluminum oxide, preferably together with Ni, Cu or Ru, are used.

Of suitability according to the invention are, for example, also Ru on aluminum oxide, silicon oxide, titanium oxide, zirconium oxide, barium oxide, calcium oxide, Ru on activated carbon, Pd on aluminum oxide, silicon oxide, titanium oxide, zirconium oxide, barium oxide, calcium oxide, Pd on activated carbon, Pt on aluminum oxide, silicon oxide, titanium oxide, zirconium oxide, barium oxide, calcium oxide or Pt on activated carbon. Support materials which can be used are also mixtures or compounds of different materials, for example clay earths or zeolites.

Also suitable according to the invention are, for example, the catalysts used in the hydrogenation.

According to the invention, the catalysts comprising at least one transition metal can also be applied to a support. These supports are, for example, metal-oxidic, basic, neutral or acidic solids which may have been treated according to the invention to increase the acid strength, for example with mineral acids such as phosphoric acid or sulfuric acid. Preference is given to using oxides or mixed oxides of B, Al, Si, Sn, Ti, Cr, Zr, Fe and Zn, which may also comprise further constituents. For example, zirconium oxide, titanium oxide, aluminum oxide, silicon oxide and combinations thereof, such as alumosilicates, such as, for example, zeolites, are suitable. Sheet silicates or natural clay earths, for example, can be used.

If the process according to the invention is carried out with heterogeneous catalysts discontinuously, then as a rule 0.1 to 50% by weight of catalyst, based on the at least one cyclic compound with Z cycles and 7 to 16 carbon atoms with a keto group is used. Preference is given to using a heterogeneous catalyst in an amount of from 0.5 to 20% by weight, particularly preferably from 1 to 10% by weight.

If the process according to stage (e1) is carried out continuously with a heterogeneous catalyst, then preferably a space velocity, i.e. the space velocity of the heterogeneous catalyst, of from 0.01 to 10 kg of at least one cyclic compound with 7 to 16 carbon atoms and one keto group/liter of catalyst/h is established. In particular, a space velocity of from 0.05 to 2 kg of at least one cyclic compound with 7 to 16 carbon atoms and one keto group/liter of catalyst/h, particularly preferably 0.1 to 1 kg of at least one cyclic compound with Z cycles and 7 to 16 carbon atoms and one keto group/liter of catalyst/h is established.

According to the invention, it is possible that the acid or the catalyst which comprises at least one transition metal is separated off in step (e2). However, within the context of the present invention, it is likewise possible that the acid or the catalyst is separated off after step (e1) and before step (e2). Possible processes for the removal are, for example, distillation, extraction, precipitation or crystallization.

According to stage (e2), the composition treated in this way is further purified by distillation, extraction and/or crystallization. Here, the distillation, extraction and/or crystallization can be carried out by all customary methods known to the person skilled in the art.

Suitable solvents for the crystallization according to stage (e2) are, for example, alcohols, ethers, hydrocarbons, aromatic hydrocarbons, ketones, preferably toluene, xylene, methanol, ethanol, propanol, butanol, acetone, diethyl ketone or methyl tert-butyl ether. According to the invention, it is likewise possible that no solvent is used, but a melt crystallization is carried out.

The distillative purification can take place in one or more columns. Here, preference is given to working at pressures between 1 and 2000 mbar. Particularly in the case of cyclic compounds with a keto group and more than 8 carbon atoms, pressures between 5 and 500 mbar are preferred, 10 to 200 mbar being particularly preferred. The temperatures (bottom temperature) are 100 to 300° C. Preferably, the temperature during distillative purification is 130 to 250° C., particularly preferably 150 to 220° C.

According to a preferred embodiment of the invention, the distillative purification is carried out at a pressure of from 1 to 2000 mbar, preferably 5 to 500 mbar, particularly preferably 10 to 200 mbar, and a bottom temperature of from 100 to 300° C., preferably 130 to 250° C., particularly preferably 150 to 220° C.

If a column is used during the distillative purification, the product of value is preferably obtained via a side takeoff. Here, it is possible according to the invention to obtain the desired product in liquid or gaseous form. Preferably high-boiling components are separated off at the bottom, and preferably low-boiling components are separated off at the top. If two columns are used, then the product of value preferably together with high-boiling components enters, preferably at the bottom, the second column, from which it can then be isolated at the top or again as side takeoff. According to the invention, it is also possible to use dividing wall columns.

In this connection, it is also possible according to the invention that further treatments take place between the individual steps of the process. In particular, it is possible according to the invention to separate off the acid or the catalyst which comprises at least one transition metal after stage (e1).

Before the distillation, extraction or crystallization according to stage (e2), it may be advantageous to remove the acid or the catalyst which comprises at least one transition metal from the composition (C) or (C') treated in stage (e), particularly if the catalyst is present in homogeneously dissolved form. In the case of heterogeneous acids or catalysts, this can take place, for example, by filtration; in the case of homogeneous acids or catalysts, for example extraction, for example with water, or a distillation are appropriate, where the acid, depending on the boiling point, is separated off at the top or at the bottom, and the catalyst is preferably separated off at the bottom.

Advantageously, the acid or the catalyst can, following removal, be reused in stage (e1). According to the invention, it is also possible that the acid or the catalyst, following removal, is subjected to an interim treatment, for example a purification, before it is reused in stage (e1).

As a result of the combination preferred according to the invention of a distillative purification, a treatment with a base, during which in particular aldehydes are attacked, and the treatment with an acid or a catalyst comprising transition metal, during which predominantly epoxides and alcohols are attacked, particularly pure products are obtained. In this connection, the process according to the invention is simple and cost-effective in terms of apparatus.

In a very particularly preferred embodiment, the process according to the invention comprises the following stages:
(a1) oxidation of a composition (A), at least comprising one cyclic olefin with Z cycles and 7 to 16 carbon atoms and at least two C—C double bonds, by means of dinitrogen monoxide to give a composition (A1), at least comprising
 the at least one cyclic compound with Z cycles and 7 to 16 carbon atoms with a keto group,
 at least one cyclic compound with Z cycles and 7 to 16 carbon atoms with at least two keto groups,
 the at least one cyclic olefin with Z cycles and 7 to 16 carbon atoms with at least two C—C double bonds,
 at least one compound with Z–1 cycles and 7 to 16 carbon atoms with at least one aldehyde group and
 dinitrogen monoxide and nitrogen,
(a1b) decompression of the composition (A1) from step (a1) in order to remove dinitrogen monoxide and nitrogen in order to obtain a composition (A1) which is essentially free from dinitrogen monoxide and nitrogen,
(a2) separating off the at least one cyclic olefin with Z cycles and 7 to 16 carbon atoms with at least two C—C double bonds from the composition (A1) from stage (a1b) in order to obtain a composition (A2), at least comprising
 the at least one cyclic compound with Z cycles and 7 to 16 carbon atoms with a keto group,
 at least one cyclic compound with Z cycles and 7 to 16 carbon atoms with at least two keto groups and
 at least one compound with Z–1 cycles and 7 to 16 carbon atoms with at least one aldehyde group, and
(b) distillative treatment of the composition (A2) from step (a2) in order to obtain a composition (B), comprising
 the at least one cyclic compound with Z cycles and 7 to 16 carbon atoms with a keto group,
 less than 0.5% by weight of the at least one cyclic compound with Z cycles and 7 to 16 carbon atoms with at least two keto groups and
 less than 1.0% by weight of the at least one compound with Z–1 cycles and 7 to 16 carbon atoms with at least one aldehyde group,
(c) hydrogenation of the composition (B) obtained from step (b) in the presence of at least one catalyst in order to obtain a composition (C) and
(e) purification of the composition (C) from step (c), at least comprising the steps
 (e1) thermal treatment of the composition (B) with at least one acid, or at least one catalyst which comprises at least one transition metal,
 (e2) further purification by a distillation,
in order to obtain a saturated cyclic compound with Z cycles and 7 to 16 carbon atoms and a keto group, in particular cyclododecanone.

The present invention is illustrated in more detail below by reference to examples.

EXAMPLES

Example 1

Oxidation of 1,5,9-Cyclododecatriene (CDT) with $N_2O$ and Separating off Unreacted 1,5,9-cyclododecatriene (Stages (a1) and (a2))

2000 g/h of 1,5,9-cyclododecatriene and 68 g/h of liquid $N_2O$ are pumped from corresponding storage containers and by means of suitable metering pumps via a static mixer into a tubular reactor (jacketed tube, wound, $\varnothing_{inside}$=6 mm, length 36 m). The tube is thermostated to 280° C. by means of heat-transfer oil, which flows in the jacket co-currently to the product, the oil outlet temperature being less than 2° C. above the oil inlet temperature. The reaction pressure is regulated to 100 bar at the reactor outlet by means of a pressure regulating valve. The conversion of 1,5,9-cyclododecatriene at the reactor outlet is 11.3%. After passing the reaction zone, the reaction mixture is decompressed in two uninsulated flash containers firstly to 3 bar and then to 60 mbar in order to take away the formed $N_2$ and unreacted $N_2O$. In so doing, the product cools to below 100° C.

The liquid product is then distilled in a packed column with at least 7 theoretical plates at a top pressure of 60 mbar ($T_{bottom}$=170° C., $T_{top}$=130° C.). The top product obtained is unreacted 1,5,9-cyclododecatriene with a purity of >99%, which is returned to the reaction again. The bottom discharge is an only slightly yellowish liquid and has a composition according to table 1:

TABLE 1

| Compound | Amount [% by wt.] |
|---|---|
| Cyclododeca-4,8-dienones | 92.0 |
| 4,8,11-Dodecatrienals | 2.3 |
| Cyclododecenediones | 2.2 |
| Cyclo-undeca-3,7-dienecarbaldehyde | 1.0 |
| 1,5,9-Cyclododecatriene | 0.4 |
| trans-12-Epoxy-cis,trans-5,9-cyclododecadiene | 0.01 |
| Dimers | 2.0 |
| Others, unidentified | Remainder to 100 |

The product is collected and used in example 2.

Example 2

Stage (b)

For the distillation of the product mixture from example 1, a continuous laboratory dividing wall column with an internal diameter of 64 mm and a length of 2.6 m (total length of the packing) is used. In preliminary experiments with test mixtures, it is ascertained that the column has 35 theoretical plates. The column is divided into three zones. The lower zone (plates 1 to 9) has a length of 0.65 m. The middle zone (plates 9 to 27) is 1.3 m in length and is divided into an inlet side and an outlet side by a dividing wall which is arranged in the middle. On the outlet side, the feed is attached at the height of plate 19. On the outlet side, the side stream product is removed in gaseous form at the height of plate 12. The upper zone (plates 27 to 35) has a length of 0.65 m. The overall column is equipped with a packing (Montz A3 750). The distillation is carried out at a top pressure of ca. 44 mbar, the pressure loss over the packing is 3.6 mbar. In order to minimize the residence time and thus the thermal stress at the bottom, the bottom evaporator used is a Sambay evaporator (wiped film evaporator). The top temperature is 137° C. and the bottom temperature is 185° C. Using a metering pump, 501 g/h of the mixture to be distilled are metered, the mixture being heated beforehand to 180° C. Via the side stream 481 g/h of product are obtained which has the composition according to table 2 (% by weight).

TABLE 2

| Compound | Amount [% by wt.] |
|---|---|
| Cyclododeca-4,8-dienones | 98.5 |
| 4,8,11-Dodecatrienals | 0.1 |
| Cyclododecenediones | 0.2 |
| Cyclo-undeca-3,7-dienecarbaldehyde | 1.1 |
| 1,5,9-Cyclododecatriene | 0.4 |
| trans-1,2-Epoxy-cis,trans-5,9-cyclododecadiene | 0.01 |

This is a colorless liquid with a melting point of +1° C.

At the bottom, 6 g/h of bottom product are obtained as a dark yellow to brown liquid with a composition according to table 3 (% by weight).

TABLE 3

| Compound | Amount [% by wt.] |
|---|---|
| Cyclododeca-4,8-dienones | 6.7 |
| Cyclododecenediones | 47.0 |
| High boilers | 46.0 |

At the top, 14 g/h of top product are obtained as a colorless liquid with the composition according to table 4 (% by weight).

TABLE 4

| Compound | Amount [% by wt.] |
|---|---|
| 4,8,11-Dodecatrienals | 76.0 |
| Cyclododeca-4,8-dienones | 9.9 |
| 1,5,9-Cyclododecatriene | 13.6 |

The stated flows are average values from a continuous distillation during which a total of 80 kg of feed are processed.

Example 3

Comparative Example

Treatment of Cyclododeca-4,8-Dienones with Base without Distillation 550 g of the bottom product from example 1 are initially introduced into a stirred flask and heated to 160° C. under protective gas (N$_2$). Then, using a syringe, 2.75 g of a 25% strength aqueous NaOH solution are added. The reaction mixture remains clear and homogeneous during this. Samples are taken at regular intervals and analyzed by means of GC. After 95 min, the solution comprises only still <30 ppm by weight of dodeca-4,8,11-trienal and 820 ppm by weight of cycloundeca-3,7-dienecarbaldehyde. The content of cyclododeca-4,8-dienone drops to 88.5% by weight. This means that ca. 4% of the product of value are destroyed during the treatment with base.

The cyclododecenediones are also degraded by the treatment with base. The cyclododecenediones are degraded and in their place bicyclic dienones are formed. Following the hydrogenation, bicyclic C$_{12}$ ketones would form therefrom; these are known to be very difficult to separate off from cyclododecanone by distillation on account of the very similar boiling point. One example is decahydroheptalenone with a boiling point of 145° C. at 15 Torr (G. Buchi, O. Jeger, Helv. Chim. Acta (1949) 32, 538). At this pressure, cyclododecanone has a boiling point of 140° C. and accordingly is very close to the boiling point of cyclododecanone.

Example 4

Treatment of Cyclododeca-4,8-dienones with Base 550 g of the side takeoff product from example 2 are initially introduced into a stirred flask and heated to 160° C. under protective gas (N$_2$). Then, using a syringe, 2.75 g of a 25% strength aqueous NaOH solution are added. The reaction mixture remains clear and homogeneous during this. Samples are taken at regular intervals and analyzed by means of GC. After 95 min, the solution comprises no dodeca-4,8,11-trienals, and only 950 ppm by weight of cycloundeca-3,7-dienecarbaldehyde. However, the content of cyclododeca-4,8-dienone drops only to 97.4% by weight. This means that only ca. 1% of the product of value is destroyed during the treatment with base (instead of 4% in example 3, comparative example).

Example 5

Comparative Example

Hydrogenation of Cyclododeca-4,8-Dienone without Prior Distillation

For the hydrogenation, a reactor cascade consisting of a tubular reactor (1.6 m in length, 20 mm internal diameter, 350 ml catalyst bed volume) with liquid circulation and an afterreactor (15 m total length, divided into 12 segments, 4 mm internal diameter, 150 ml catalyst bed volume) is used, with both reactors being provided with a jacket via which a heat transfer oil is circulated for the purpose of thermostating. The reactors are filled with a Pd (0.2% by weight) on aluminum oxide catalyst (3 mm strands, Pd as aqueous palladium nitrate solution soaked on to a commercial aluminum oxide support, then dried and calcined in the air at 300° C.). In this plant, the bottom product from example 1 is hydrogenated at 130° C. and a hydrogen pressure of 30 bar, with 3 mol of hydrogen/mole of feed, which is calculated as 100% cyclododeca-4,8-1-one, being used. The reactors are operated in trickle mode. The ratio of liquid circulation to feed in the first reactor is 10:1 and the total space velocity is 0.5 kg of feed/liter of catalyst/h. Both liquid and gaseous feed are introduced first into the main reactor. Both the liquid and the gaseous discharge from the main reactor are then passed directly to the afterreactor. The hydrogenation is operated for 300 h. The hydrogenation discharge has the composition according to table 5 (% by weight).

TABLE 5

| Compound | Amount [% by weight] |
|---|---|
| Cyclododecanone | 91.5 |
| Cyclododecenones | 0.3 |
| Cyclododecanol | 0.2 |
| Dodecanal | 1.9 |
| 1-Dodecanol | 0.2 |
| Cycloundecanecarbaldehyde | 0.7 |
| Hydroxymethylcycloundecane | 0.2 |
| Other compounds, unidentified | In each case <0.1, total remainder to 100 |

This product is then passed over an acidic titanium dioxide (1.5 mm strands, pure titanium dioxide to more than 99% in the anatase form as described in WO 2007/104650, 315 ml catalyst bed volume, tubular reactor with a length of 1.5 m, heating by external oil heating mantle) at 200° C. and atmospheric pressure (space velocity ca. 0.5 kg of feed/liter of catalyst/h). This discharge is collected and 3 kg of it are subjected to fractional distillation in a distillation boiler with attached column (1 m packed column). The fraction (0.5 kg) with the highest cyclododecanone purity (99.5% by weight) (ca. 50 mbar distillation pressure, ca. 165° C. boiling point) also comprises the secondary components according to table 6 (% by weight):

TABLE 6

| Compound | Amount [% by weight] |
|---|---|
| Cyclododecenones | 0.3 |
| Cycloundecanecarbaldehyde | 0.02 |
| Hydroxymethylcycloundecane | 0.01 |
| Other compounds, unidentified | In each case <0.05, total remainder to 100 |

Example 6

Hydrogenation of Cyclododeca-4,8-Dienone with Prior Distillation

Example 5 is repeated except that the starting material used is the side takeoff product from example 2. The hydrogenation discharges have the composition according to table 7 (% by weight).

TABLE 7

| Compound | Amount [% by weight] |
|---|---|
| Cyclododecanone | 98.4 |
| Cyclododecanol | 0.1 |
| Dodecanal | 0.05 |
| 1-Dodecanol | 0.04 |
| Cycloundecanecarbaldehyde | 0.8 |
| Hydroxymethylcycloundecane | 0.2 |
| Other compounds, unidentified | In each case <0.05, total remainder to 100 |

This product is then passed over acidic titanium dioxide at 200° C. and atmospheric pressure (space velocity ca. 1 kg of feed/liter of catalyst/h). This discharge is collected and 3 kg of it are subjected to fractional distillation in a distillation boiler with attached column. The fraction (2.5 kg) with the highest cyclododecanone purity (99.9% by weight) also comprises the secondary components according to table 8 (% by weight):

TABLE 8

| Compound | Amount [% by weight] |
|---|---|
| Cycloundecanecarbaldehyde | 0.01 |
| Hydroxymethylcycloundecane | 0.01 |
| Other compounds, unidentified | In each case <0.005, total remainder to 100 |

Example 7

Oxidation of 1,5-cyclooctadiene with $N_2O$ 1,5-Cyclooctadiene (commercial product, Aldrich at least 99% redistilled, 700 ml) was poured into a 1.2 l autoclave, the autoclave was closed and rendered inert with $N_2$. The autoclave was flushed three times with 50 bar $N_2$ and is then pressurized with $N_2O$ without stirrer movement to 50 bar cold pressure. The stirrer was switched on, adjusted to 400 rpm and then heated to the desired temperature (200° C.) for 24 h. After 24 h, the autoclave was cooled to room temperature and decompressed to ambient pressure. The process of being rendered inert, of the $N_2O$ addition, of the heating to 200° C. and of the decompression was then repeated two more times. Discharge:

TABLE 9

| Compound | Amount [area %] |
|---|---|
| 1,5-Cyclooctadiene (starting material) | 17.8 |
| Cyclooct-4-en-1-one | 34.1 |
| 1,5-Cyclooctadione | 21.5 |
| 3a-Hydroxyhexahydropentalen-1-one | 18.4 |
| (Z)-Octa-4,7-dienal | 0.19 |
| Cyclohept-4-enecarbaldehyde | 0.16 |
| Other compounds (including dimers), unidentified | In each case <0.2, total remainder to 100 |

Example 8

Oxidation of Cyclotetradeca-1,8-Diene

Cyclotetradeca-1,8-diene (isomer mixture, ca. 91%, 2 g) and cyclohexane (98 g) were poured into a 300 ml autoclave, the autoclave was closed and rendered inert with $N_2$. The autoclave was flushed three times with 50 bar $N_2$ and then pressurized with N₂O without stirrer movement to 30 bar cold pressure. The stirrer was switched on, adjusted to 400 rpm and then heated to the desired temperature (280° C.). After 24 h, the autoclave was cooled to room temperature, decompressed to ambient pressure and the product was analyzed by GC.

Discharge:

TABLE 10

| Compound | Amount [area % minus solvent] |
| --- | --- |
| Cyclotetradeca-1,8-diene (starting material, 2 iso.) | 11.2 |
| Cyclotetradec-7-en-1-one (2 iso.) | 12.1 |
| Cyclotetradeca-1,7-dione | 29.1 |
| Cyclotetradeca-1,8-dione | 27.6 |
| Tetradeca-1,8-dienal | 1.7 |
| Cyclotridec-7-enecarbaldehyde | 1.2 |
| Other compounds, unidentified | In each case <0.5, total remainder to 100 |

Example 9

Oxidation of cyclohexadeca-1,9-diene

Cyclohexadeca-1,9-diene (isomer mixture, ca. 89%, 2.1 g) and cyclohexane (98.5 g) were poured into a 300 ml autoclave, the autoclave was closed and rendered inert with $N_2$. The autoclave was flushed three times with 50 bar $N_2$ and is then pressurized with $N_2O$ without stirrer movement to 30 bar cold pressure. The stirrer was switched on, adjusted to 400 rpm and then heated to the desired temperature (240° C.). After 24 h, the autoclave was cooled to room temperature, decompressed to ambient pressure and the product was analyzed by GC.

Discharge:

TABLE 11

| Compound | Amount [area % without solvent] |
| --- | --- |
| Cyclohexadeca-1,9-diene (starting material, 3 iso.) | 21.6 |
| Cyclohexadec-8-en-1-one (2 iso.) | 33.7 |
| Cyclohexadecanedione (2 iso.) | 13.6 |
| Hexadeca-8,15-dienal | 1.0 |
| Other compounds, unidentified | In each case <0.2, total remainder to 100 |

The invention claimed is:

1. A process for preparing at least one cyclic compound with Z cycles and 7 to 16 carbon atoms with a keto group, at least comprising the stages:
   (a1) oxidation of a composition (A), at least comprising one cyclic olefin with Z cycles and 7 to 16 carbon atoms and at least two C—C double bonds, by means of dinitrogen monoxide to give a composition (A1), at least comprising
      the at least one cyclic compound with Z cycles and 7 to 16 carbon atoms with a keto group,
      the at least one cyclic olefin with Z cycles and 7 to 16 carbon atoms with at least two C—C double bonds and
      at least one compound with Z−1 cycles and 7 to 16 carbon atoms with at least one aldehyde group,
   (a2) separating off the at least one cyclic olefin with Z cycles and 7 to 16 carbon atoms with at least two C—C double bonds from the composition (A1) from stage (a1) in order to obtain a composition (A2), at least comprising
      the at least one cyclic compound with Z cycles and 7 to 16 carbon atoms with a keto group and
      at least one compound with Z−1 cycles and 7 to 16 carbon atoms with at least one aldehyde group, and
   (b) distillative treatment of the composition (A2) from step (a2) in order to obtain a composition (B), comprising
      the at least one cyclic compound with Z cycles and 7 to 16 carbon atoms with a keto group and
      less than 1.0% by weight of the at least one compound with Z−1 cycles and 7 to 16 carbon atoms with at least one aldehyde group,
   where Z can be 1, 2, 3 or 4.

2. The process according to claim 1, which comprises at least the following stages:
   (a1) oxidation of a composition (A), at least comprising one cyclic olefin with Z cycles and 7 to 16 carbon atoms and at least two C—C double bonds, by means of dinitrogen monoxide to give a composition (A1), at least comprising
      the at least one cyclic compound with Z cycles and 7 to 16 carbon atoms with a keto group,
      at least one cyclic compound with Z cycles and 7 to 16 carbon atoms with at least two keto groups,
      the at least one cyclic olefin with Z cycles and 7 to 16 carbon atoms with at least two C—C double bonds and
      at least one compound with Z−1 cycles and 7 to 16 carbon atoms with at least one aldehyde group,
   (a2) separating off the at least one cyclic olefin with Z cycles and 7 to 16 carbon atoms with at least two C—C double bonds from the composition (A1) from stage (a1) in order to obtain a composition (A2), at least comprising
      the at least one cyclic compound with Z cycles and 7 to 16 carbon atoms with a keto group,
      at least one cyclic compound with Z cycles and 7 to 16 carbon atoms with at least two keto groups and
      at least one compound with Z−1 cycles and 7 to 16 carbon atoms with at least one aldehyde group, and
   (b) distillative treatment of the composition (A2) from step (a2) in order to obtain a composition (B), comprising
      the at least one cyclic compound with Z cycles and 7 to 16 carbon atoms with a keto group,
      less than 0.5% by weight of the at least one cyclic compound with Z cycles and 7 to 16 carbon atoms with at least two keto groups and
      less than 1.0% by weight of the at least one compound with Z−1 cycles and 7 to 16 carbon atoms with at least one aldehyde group.

3. The process according to claim 1, wherein stage (b) is followed by at least the following stage (c):
   (c) hydrogenation of the composition (B) in the presence of at least one catalyst in order to obtain a composition (C).

4. The process according to claim 1, wherein stage (b) is followed by at least the following stage (d):
   (d) treatment of the composition (B) with at least one base in order to obtain a composition (D).

5. The process according to claim 4, wherein stage (d) is followed by at least the following stage (c'):
   (c') hydrogenation of the composition (D) in the presence of at least one catalyst in order to obtain a composition (C').

6. The process according to claim 3, wherein stage (c) or (c') is followed by at least the stage (e):
  (e) purification of the composition (C) from step (c) or (C') from step (c), at least comprising the steps
    (e1) thermal treatment of the composition (C) or (C') with at least one acid, or at least one catalyst which comprises at least one transition metal,
    (e2) further purification by a process selected from the group consisting of distillation, extraction and crystallization.

7. The process according to claim 1, wherein the cyclic olefin is cyclododecatriene.

8. The process according to claim 1, wherein the cyclic olefin is cyclododecatriene which has been prepared by trimerization of butadiene.

9. The process according to claim 1, wherein the at least one cyclic olefin with Z cycles and 7 to 16 carbon atoms and at least two C—C double bonds is selected from the group consisting of 1,5-cyclooctadiene, 1,5-cyclododecadiene, 1,9-cyclohexadecadiene, 1,8-cyclotetradecadiene, 1,6-cyclododecadiene, 1,6,11-cyclopentadecatriene, 1,5,9-cyclododecatriene, vinylcyclohexene, norbornadiene, ethylidenenorbornene and mixtures thereof.

10. The process according to claim 4, wherein the base is selected from the group consisting of sodium hydroxide, potassium hydroxide and mixtures thereof.

* * * * *

UNITED STATES PATENT AND TRADEMARK OFFICE
CERTIFICATE OF CORRECTION

PATENT NO. : 8,188,320 B2
APPLICATION NO. : 12/694815
DATED : May 29, 2012
INVENTOR(S) : Teles et al.

It is certified that error appears in the above-identified patent and that said Letters Patent is hereby corrected as shown below:

In Claim 6 (col. 39, l. 4), delete "(c)," and insert --(c'),-- therefor.

Signed and Sealed this
Twenty-eighth Day of August, 2012

David J. Kappos
*Director of the United States Patent and Trademark Office*